US007850949B2

(12) United States Patent
Fang

(10) Patent No.: US 7,850,949 B2
(45) Date of Patent: Dec. 14, 2010

(54) PURIFICATION OF SYNTHETIC OLIGOMERS

(75) Inventor: Shiyue Fang, Houghton, MI (US)

(73) Assignee: Michigan Technological University, Houghton, MI (US)

(*) Notice: Subject to any disclaimer, the term of this patent is extended or adjusted under 35 U.S.C. 154(b) by 117 days.

(21) Appl. No.: 11/865,499

(22) Filed: Oct. 1, 2007

(65) Prior Publication Data

US 2008/0081902 A1 Apr. 3, 2008

Related U.S. Application Data

(60) Provisional application No. 60/827,592, filed on Sep. 29, 2006.

(51) Int. Cl.
*A61K 8/55* (2006.01)
(52) U.S. Cl. .......................................... 424/57
(58) Field of Classification Search ................. None
See application file for complete search history.

(56) References Cited

U.S. PATENT DOCUMENTS

| 3,712,936 | A | * | 1/1973 | Jelinek ..................... 558/171 |
| 6,692,912 | B1 | | 2/2004 | Boles et al. |
| 6,921,818 | B2 | * | 7/2005 | Sproat ..................... 536/26.6 |
| 7,125,945 | B2 | | 10/2006 | Shah |
| 2003/0195351 | A1 | * | 10/2003 | Pieken et al. ............... 536/25.3 |
| 2006/0178507 | A1 | | 8/2006 | Berry et al. |

FOREIGN PATENT DOCUMENTS

| WO | 03/018616 | | 3/2003 |
| WO | 2004/002995 | | 1/2004 |
| WO | WO-2004/002995 | * | 1/2004 |
| WO | WO 2005/035588 | | 4/2005 |
| WO | WO-2005/087818 | * | 9/2005 |
| WO | WO 2006/113792 | | 10/2006 |
| WO | 2008/067026 | | 6/2008 |

OTHER PUBLICATIONS

Adamczyk, M. et al., "Synthesis of biological markers in fossil fuels. 2. Synthesis and 13C NMR studies of substituted indans and tetralins," J. Org. Chem. (1984) 49:4226-4237.
Atkinson, R.C. et al., "The syntheses and catalytic applications of unsymmetrical ferrocene ligands," Chem. Soc. Rev. (2004) 33:313-328.
Banfield, S.C. et al., "Unexpected reactivity of the Burgess reagent with thiols: synthesis of symmetrical disulfides," J. Org. Chem. (2007) 72(13):4989-4992.
Bondinell, W.E. et al., "Inhibitors of phenylethanolamine N-methyltransferase and epinephrine biosynthesis. 1. Chloro-substituted 1,2,3,4-tetrahydroisoquinolines," J. Med. Chem. (1980) 23:506-511.
Burgler. F.W. et al., "Stereoselective addition reactions with chalcogen electrophiles," Archive for Org. Chem. (2007) x:21-28.

Colacot, T.J., "A concise update on the applications of chiral ferrocenyl phosphines in homogeneous catalysis leading to organic synthesis," Chem. Rev. (2003) 103:3101-3118.
Crooke, S.T., "Progress in antisense technology," Annu. Rev. Med. (2004) 55:61-95.
Curnow, O.J. et al., "Synthesis, structures and raclmeso isomerization behaviour of bisplanar chiral bis(phosphino-η5-indenyl)iron(II) complexes," J. Organomet. Chem. (2004) 689:1897-1910.
Curnow, O.J. et al., "Facile meso to rac isomerization of the bisplanar chiral ferrocenyldiphosphine bis(1-(diphenylphosphino)-η5-indenyl)iron(II)," Organometallics (2002) 21:2827-2829.
Curnow, O.J. et al., "Mechanistic studies on a facile ring-flipping process in planar chiral ferrocenes under ambient and high pressure and its relevance to asymmetric catalysis," Organometallics (2004) 23:906-912.
Dai, L.X. et al., "Assymmetric catalysis with chiral ferrocene ligands," Acc. Chem. Res. (2003) 36:659-667.
Fang, S. et al., "Fluoride-cleavable biotinylation phosphoramidite for 5'-end-labeling and affinity purification of synthetic oligonucleotides," Nuc. Acids Res. (2003) 31(2):708-715.
Fang, S. et al., "Reversible 5'-end biotinylation and affinity purification of synthetic RNA," Tetrahedron Letters (2004) 45:7987-7990.
Fang, S. et al., "Reversible biotinylation of the 5'-terminus of ligodeoxyribonucleotides and its application in affinity purification," Curr. Protocols in Nucleic Acid Chem. (2003) 4.20.1-4.20.17.
Fang, S. et al., "Reversible biotinylation phosphoramidite for 5'-end-labeling, phosphorylation, and affinity purification of synthetic oligonucleotides," Bioconjugate Chem. (2003) 14:80-85.
Farrugia, L.J., "ORTEP-3 for Windows—a version of ORTEP-III with a graphical user interface (GUI)," J. Appl. Cryst. (1997) 30:565.
Fu, G.C., "Asymmetric catalysis with 'planar-chiral' derivatives of 4-(dimethylamino)pyridine," Acc. Chem. Res. (2004) 37:542-547.
Gong, J-X. et al., "Total synthesis of gymnorrhizol, an unprecedented 15-membered macrocyclic polydisulfide from the Chinese mangrove Bruguiera gymnorrhiza," J. Org. Lett. (2007) 9(9):1715-1716.
Hajipour, A.R. et al., "Oxidation of thiols with methyltriphenylphosphonium dichromate (MTPPD) in dichloromethane at room temperature," J. Sulfur Chem. (2006) 27(5):441-444.
Hauser, F.M. et al., "Ketone transposition: 2(1H)-tetralones from 1(2H)-tetralones," Synthesis-Stuttgart (1980) 621-623.
Imanishi, T. et al., "BNAs: novel nucleic acid analogs with a bridged sugar moiety," Chem. Commun. (2002) 1653-1659.
Ishikawa, F. et al., "Cyclic guanidines. XVI. Synthesis and biological activities of tetracyclic imidazo[2,1-b]quinazolinine derivatives," Chem. & Pharm. Bull. (1985) 33:3336-3348.

(Continued)

*Primary Examiner*—Cecilia Tsang
*Assistant Examiner*—Satyanarayana R Gudibande
(74) *Attorney, Agent, or Firm*—Michael Best & Friedrich LLP

(57) ABSTRACT

This invention provides a novel method for purifying synthetic oligomers comprising capping, polymerizing and separating any failure sequences produced during oligomer synthesis. Either the failure sequence or the full-length oligomer may be polymerized. Optionally, small molecule impurities may also be incorporated into the polymerized material. The invention provides novel capping agents having a polymerizable functional group. The invention also provides kits comprising at least one composition of the present invention.

1 Claim, 16 Drawing Sheets

OTHER PUBLICATIONS

Ma, H.C. et al., "Synthesis of iminoquinones from anilines using IBX in DMSO," Synthesis (2007) 3:412-416.

Maier, T.C. et al., "Catalytic enantioselective O-H insertion reactions," J. Am. Chem. Soc. (2006) 128:4594-4595.

Olejnik, J. et al., "Photocleavable biotin phosphoramidite for 5'-end-labeling, affinity purification and phosphorylation of synthetic oligonucleotides," Nuc. Acids Res. (1996) 24(2):361-366.

Pearson, W.H. et al., "Fluorous affinity purification of oligonucleotides," J. Org. Chem. (2005) 70:7114-7122.

Ruble, J.C. et al., "Chiral π-complexes of heterocycles with transition metals: a versatile new family of nucleophilic catalysts," J. Org. Chem. (1996) 61:7230-7231.

Sathe, M. et al., "Oxidation of thiols to disulfides using silica chloride as heterogeneous catalyst," Chemistry Letters (2006) 35(9):1048-1049.

Schulte, M. et al., "Purification of DMT-on oligonucleotide by simulated moving-bed (SMB) chromatography," Org. Process Res & Dev. (2005) 9:212-215.

Shintani, R. et al., "Copper-catalyzed enantioselective conjugate addition of diethylzinc to acyclic enones in the presence of planar-chiral phosphaferrocene-oxazoline ligands," Org. Lett. (2002) 4:3699-3702.

Siemeling, U. et al., "1,1'-di(heteroatom)-functionalised ferrocenes as [N,N], [O,O] and [S,S] chelate ligands in transition metal chemistry," Chem. Soc. Rev. (2005) 34:584-594.

Sobik, P. et al., "Identification, synthesis, and conformation of tri- and tetrathiacycloalkanes from marine bacteria," J. Org. Chem. (2007) 72(10):3776-3782.

Sproat, B.S. et al., "Fast and simple purification of chemically modified hammerhead ribozymes using a lipophilic capture tag," Nuc. Acids Res. (1999) 27(8):1950-1955.

Trost, B.M. et al., "Asymmetric transition-metal-catalyzed allylic alkylations: applications in total synthesis," Chem. Rev. (2003) 103:2921-2943.

Trost, B.M., "Asymmetric catalysis an enabling science," Proc. Natl. Acad. Sci. USA (2004) 101:5348-5355.

Vester, B. et al., "LNC (Locked Nucleic Acid): High-affinity targeting of complementary RNA and DNA," Biochem. (2004) 43(42):13233-13241.

Wilson, C. et al., "Building oligonucleotide therapeutics using non-natural chemistries," Curr. Opin. Chem. Biol. (2006) 10:607-614.

Yavari, I. et al., "Conversion of thiols to disulfides using a hexamethylenetetramine-bromine complex," Phosphorus, Sulfur and Silicon and the Related Elements, (2006) 181(11):2659-2662.

Fang, S., "Simple methods for oligonucleotide purification," National Science Foundation Award Abstract #0647129 (2007) 2 pages—Retrieved from the Internet: http://www.nsf.gov/awardsearch/showaward.do?awardnumber=0647129, retrieved on May 6, 2008.

International Search Report and Written Opinion of the International Searching Authority for Application No. PCT/US2007/080099 dated May 8, 2008 (12 pages).

* cited by examiner

PURIFICATION OF SYNTHETIC OLIGOMERS

CROSS-REFERENCE TO RELATED APPLICATIONS

This application claims priority under 35 U.S.C. §119(e) to U.S. Provisional Patent Application No. 60/827,592 filed Sep. 29, 2006, which is hereby incorporated by reference.

INTRODUCTION

Synthetic oligonucleotides have wide applications in biology and medicine. With one oligonucleotide drug on the market and more than 40 others in various stages of clinical trials, the interest in using oligonucleotides as therapeutic agents continues to grow. This growing demand requires large quantities of oligonucleotides. For many purposes, including use as therapeutic agents to cure human diseases, these crude oligonucleotides must be purified to remove the failure sequences generated in the coupling steps in the synthesis. Currently used purification methods include gel electrophoresis, HPLC and others—all of which are expensive, labor intensive and unsuitable for large scale purification. The most frequently used purification methods such as gel electrophoresis are not suitable for large scale purification. Reverse phase and ion exchange HPLC have been adapted to large scale purification, but there are high costs associated with instrumentation, eluents (including their evaporation) and columns. Other known purification methods are also not ideal. Consequently, the development of highly efficient and low cost methods for large scale production of oligonucleotides is desired.

SUMMARY OF THE INVENTION

The present invention provides a method of purifying oligomers comprising capping any failure sequences produced during synthesis with a capping agent having a polymerizable functional group, polymerizing the capped failure sequences; and separating the polymerized material from the full-length oligomer.

The present invention also provides a method of purifying an oligomer comprising attaching a polymerizable functional group to an end of a full length oligomer, polymerizing the full length oligomers, removing the failure sequences from the polymerized full length oligomers, and recovering the full length oligomers.

In addition, the present invention provides capping agents comprising polymerizable functional groups and its for purifying oligomers.

DETAILED DESCRIPTION OF THE INVENTION

Figure 1:
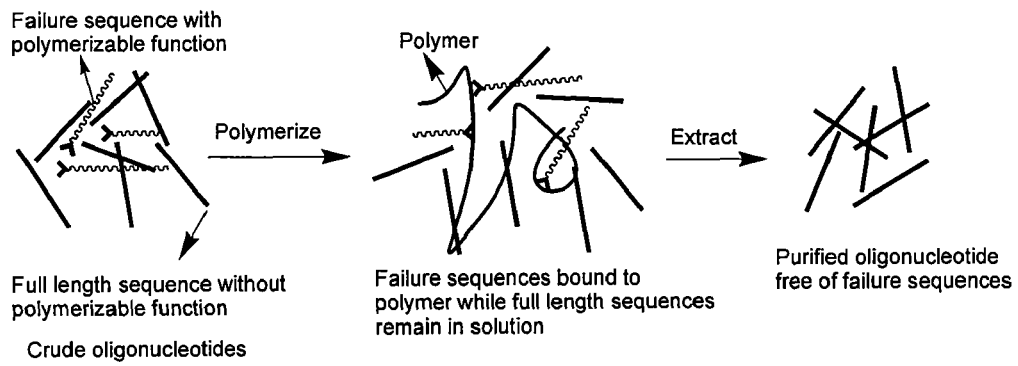
FIG. 1 illustrates one method for oligonucleotide purification. Unwanted failure sequences contain polymerizable function, while the desired full length sequences do not. After polymerization, failure sequences are incorporated into a polymer, and full length sequences are isolated by simple extraction.

The present invention includes a method of purifying synthetic oligomers via a polymerization technique, capping agents having a polymerizable functional group, and kits for purifying oligomers comprising a capping agent having polyerizable functional group. Synthesis of oligomers generally proceeds in a step-wise manner with each monomer being added in sequence to the ends of a plurality growing oligomer. After synthesis and deprotection/cleavage, crude oligomers normally contains the following impurities:

(i) Truncated failure sequences. These impurities result from the coupling steps of the synthesis. For a successful 20-mer synthesis, these impurities comprise about 30% of the oligonucleotide content of the crude mixture. They have similar physical properties as the desired full length sequences, and so are difficult to remove. They are usually capped with acetic anhydride in the synthesis. As a result, if the 5'-OH DMTr (4,4'-dimethoxytrityl) protecting groups in the last synthesis cycle are not removed, then after basic deprotection and cleavage, the full length sequences have the hydrophobic DMTr group on their 5'-end while the failure sequences do not (acyl groups on the failure sequences are removed under deprotection conditions). This is the basis of DMTr-on reverse phase HPLC purification. Although this is the most widely used oligonucleotide purification method, it is very costly for large scale production.

(ii) Small organic impurities. These result from the phosphate and exo-amino protecting groups which include acrylonitrile, benzamide, acetamide and isobutyramide and others depending on which protecting groups are used. Because of their very different physical properties from oligonucleotides, they can be removed by precipitation from aqueous buffer with ethanol or 2-propanol.

(iii) Other oligonucleotide impurities. These are very difficult to remove; fortunately, only very limited quantities are typically present. Two examples are N+1 and N+2 sequences, which result from double coupling due to the mild acidity of activating agents that causes premature detritylation in the coupling step. They can be troublesome to remove even on small scale. When the DMTr-on reverse phase HPLC strategy is used, they also contain a 5'-DMTr group. Ion exchange HPLC cannot resolve a single nucleotide difference for a typical 20-mer. Gel electrophoresis can do the job but can only on a very small scale. Additional impurities are acrylonitrile-oligonucleotide adducts. In addition, for oligophosphorothioate synthesis, because of incomplete sulfurization, impurities such as $(P=O)_1$ and $(P=O)_2$ mers exist, they can be kept to a minimum amount by using a more efficient sulfurization agent.

These impurities need to be separated from the desired full-length oligomer when synthesis is complete. The present invention contemplates the purification of oligomers through the use of capping agents containing polymerizable functional groups. Both failure sequences and small organic impurities can be removed using the method of the present invention.

As used herein, "oligomer" includes oligonucleotides, modified oligonucleotides, polynucleotides, modified polynucleotides, oligosaccharides, modified oligosaccharides, polysaccharides, modified polysaccarides, peptides, modified peptides, polypeptides, modified polypeptides, and any conjugates of two or more of these different types of oligomers such as peptide nucleic acid conjugates and glycopeptides. Modified oligomers include peptide nucleic acids, locked DNA, phosphotihioate oligonucleotides, beta-peptides and quaternary peptides. Modifications to oligosaccharides include alterations of ring size, ring atoms and various substitutions on the sugar rings. One of ordinary skill in the art can envision other modified oligomers which fall within the scope of the present invention. Oligomers may contain both natural and unnatural monomers. For example, both D- and L-amino acids can be used. The term "oligomer" is not intended to be limited to any specific number of monomers. Instead, it is meant to encompass an oligomer (or polymer) of any length that can be made by a step-wise process.

As used herein, "failure sequence" means an oligomer to which the next monomer did not attach during synthesis. Thus, a failure sequence of any given step in the synthesis contains all monomers except for the most recently added monomer.

As used herein, "lower alkyl" means an alkyl group of 1 to 4 carbon atoms, that may be branched, such as methyl, ethyl, propyl, isopropyl and butyl.

The oligomer purification methods of the present invention are suitable for both large and small scale purification. Oligomers purified by the methods of the present invention are substantially free of failure sequences and have similar or better quality than those purified by DMTr-on reverse phase HPLC method. The purified oligomer may be of greater than about 90% purity, or greater than about 95%, or greater than about 97%, or greater than about 99% or greater than about 99.5%. By "substantially free", it is meant that the oligomer contains less than about 5% by weight of failure sequences, or less than about 3%, or less than about 1% or less than about 0.5%.

In one embodiment of the present invention, simple phosphorous compounds that contain functional groups capable of polymerizing in the presence of an initiator and/or a polymerization partner are used as capping agents (in place of the commonly used acetic anhydride) during oligomer synthesis to block failure sequences. Thus, all unwanted failure sequences contain the polymerizable functions, while the desired full length sequences do not. After synthesis, failure sequences are incorporated into a polymerized material, and the full length oligomers remain in solution or in the polymer matrix and are separated from the polymerized material using any technique known to one of ordinary skill in the art including extraction with buffer and filtration. If the oligomer is synthesized on a solid support, the oligomer can be cleaved from the solid support prior to polymerization. (See FIG. 1).

Figure 2:
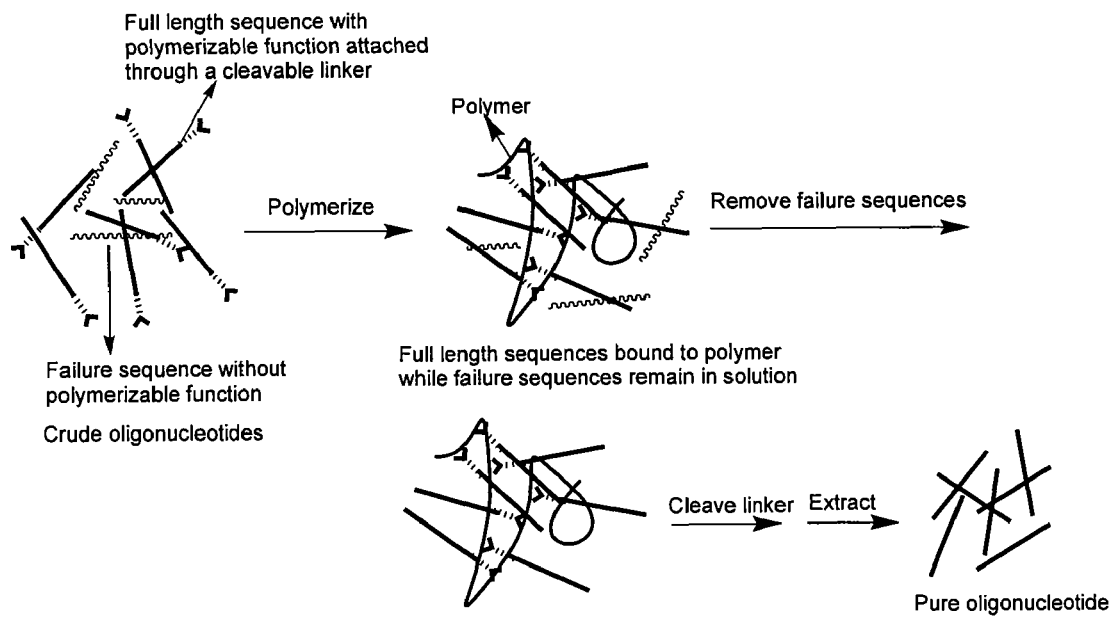
FIG. 2 illustrates an additional method for oligonucleotide purification. Desired full length sequences contain polymerizable function, while unwanted sequences do not. After polymerization, full length sequences are incorporated into a polymer, failure sequences are removed by washing, and full length sequences are cleaved from the polymer and extracted with a buffer.

In another embodiment of the present invention, polymerizable functional groups are incorporated onto the end of the full length sequences in the last step of oligomer synthesis. Because failure sequences are capped with a standard capping agent, such as acetic anhydride, dimethyl-formanide, diethylene glycol monoethyl ether phosphoramidite, or bis(1,1,1,3,3,3-hexafluoro-2-propyl)-2-propyl phosphate, in each synthetic cycle, only the full length sequence contains the polymerizable functional group. Once the full length sequences are incorporated into a polymerized material, the failure sequences are removed by simple washing because they do not contain a polymerizable functional group, and then, full length sequences are recovered from the polymerized material using a cleavage reagent. (See FIG. 2). If the synthesis occurs on a solid support, the oligomer can be cleaved from the solid support before or after polymerization.

Using either of these methods, the small molecules resulted from deprotection of nucleobases and phosphate groups can also be removed if suitable polymerizable functions are incorporated into the protecting groups. When the first method is used, the small molecules resulted from deprotection will be incorporated into the polymerized material in the same fashion as the failure sequences are incorporated. When the second method is used, the small molecules resulted from deprotection will also be incorporated into the polymerized material. However, the full length sequence can be cleaved from the polymerized material and the small molecule impurities cannot because there is no cleavable linker in them.

Polymerization reactions suitable for the methods of the present invention have one or more of the following characteristics: (i) the polymerization reaction is highly efficient once initiated; (ii) the reaction tolerates moisture and air and, suitably, can be performed in aqueous buffer; (iii) oligomers are stable under the polymerization conditions; and (iv) the polymerizable functional groups are easily accessible and are stable under oligomer synthesis conditions.

Reactions that are suitable for oligonucleotide purification include, but are not limited to, the radical acrylamide polymerization reaction, the thiol oxidation to disulfide reaction, the Sharpless "click" reaction, the Grubbs aqueous ROMP reaction, the conjugate addition reaction between maleimide and thiol, and the amide bond formation reaction between carboxylic acid esters and alkyl amines. Reactions that are suitable for oligosaccharide and peptide purification include, but are not limited to, the Sharpless "click" reaction.

Radical Acrylamide Polymerization

Figure 3:
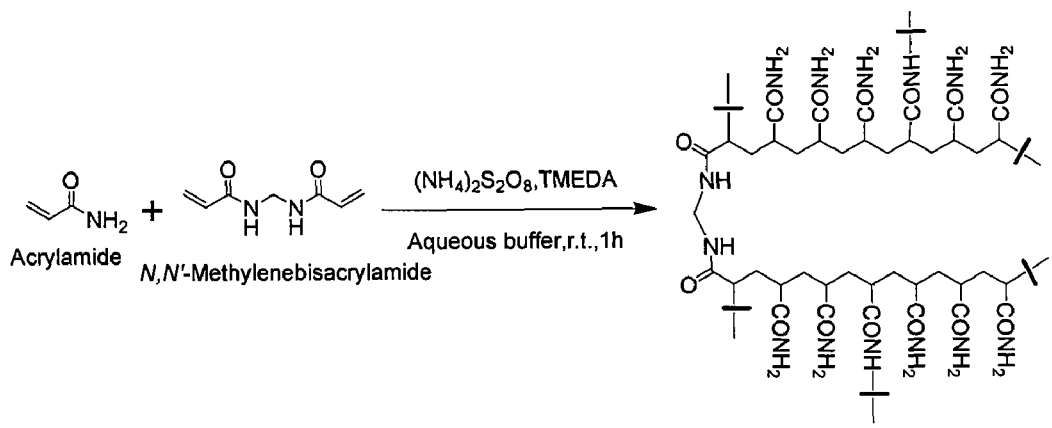
FIG. 3 represents the chemical reaction for formation of polyacrylamide gel.

The general acrylamide polymerization reaction is shown in FIG. 3. The materials for this reaction are inexpensive, and the reaction is highly efficient and can be performed in aqueous buffer open to air at room temperature. In addition, acrylamide functionalities are stable under oligonucleotide synthesis and deprotection/cleavage conditions using phosphoramidite chemistry. Appropriate polymerization conditions can be readily determined by one of ordinary skill in the art. Suitable conditions include $(NH_4)_2S_2O_8$/TMEDA/water at room temperature for about 1 hour. For example, for a 1 mmol oligonucleotide synthesis, optionally about 10 mmol to about 100 mmol acrylamide, optionally about 0.2 mmol to about 2.0 mmol N,N'-methylene-bisacrylamide, about 1 μmol to about 10 tμmol $(NH_4)_2S_2O_8$, and about 1 μmol to about 10 μmol TMDEA may be used.

Suitable capping agents for purification using radical acrylamide polymerization include compounds of formula (I):

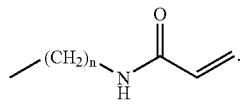
(I)

wherein $R_1$ is halogen, such as Cl, Br, or F or a secondary amine group, such as

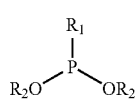

$R_2$ is independently selected from lower alkyl,

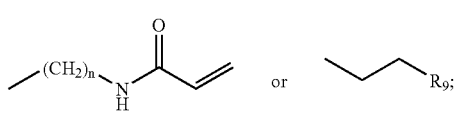

n is an integer from 1 to 5;

$R_9$ is an electron withdrawing group such as cyano, $COOR_{10}$, $SO_2Ph$ and $NO_2$;
$R_{10}$ is lower alkyl; and
at least one $R_2$ is

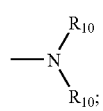

Suitably, the capping agent contains more than one polymerizable functional group. It is hypothesized that additional polymerizable functional groups on the capping agent increase the likelihood that capped polymers will be incorporated into the polymer.

However, capping agents containing only one polymerizable functional group have the advantage of more stable under basic deprotection/cleavage conditions when the other $R_2$ is a removable group such as 2-cyanoethyl group.

When $R_1$ is a secondary amino group, the capping agents for radical acrylamide polymerization require the use of an activating agent. The most commonly used activating agent is 1H-tetrazole. Other suitable activating agents include, but are not limited to 4,5-dicyanoimidazole, 5-(4-nitrophenyl)-1H-tetrazole, 5-methylthio-1H-tetrazole, 5-ethylthio-1H-tetrazole, ethylthiotetrazole, and 5-benzylmercapto-1H-tetrazole.

Optionally, when $R_1$ is a halogen atom, a base may be added to neutralize acid produced during the capping reaction. The base may be an amine base such as trimethylamine, pyridine, diazobicyclo base, or 5-methoxybenzimidazole.

Figure 4:
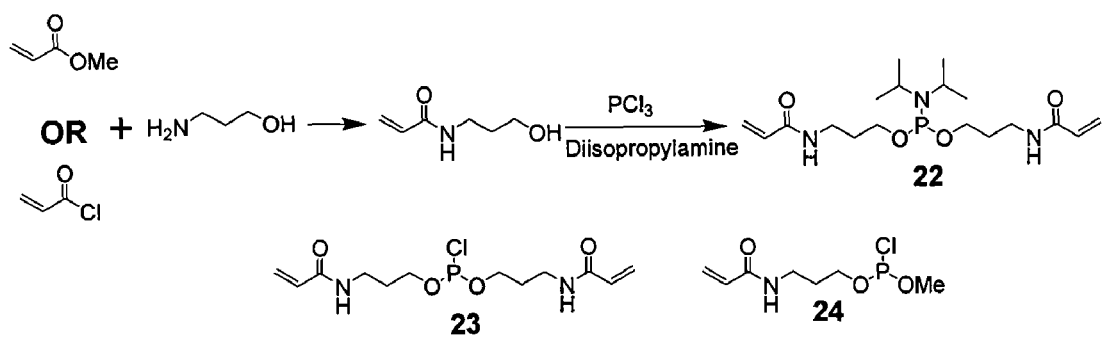
FIG. 4 represents the chemical reaction for synthesis of the capping agents 22-24.

Syntheses of suitable phosphorous capping agents 22-24 (shown below) are shown in FIG. 4.

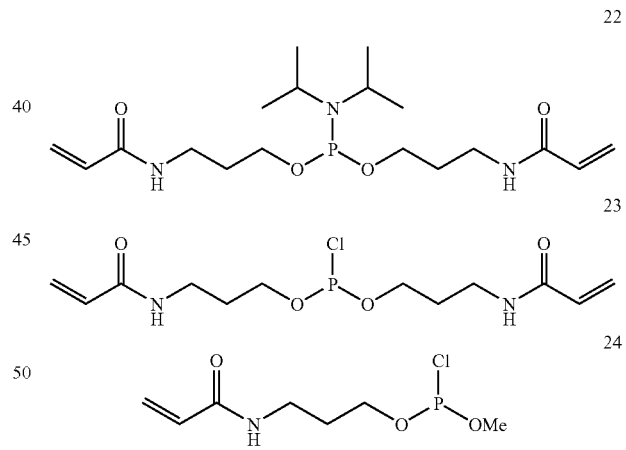

Compounds 22 and 23 contain two polymerizable functional groups, which can increase the likelihood that failure sequences will be incorporated into the polymer. Compound 24 contains only one polymerizable functional group. When compound 22 is used for capping, an activator is required. If 23 or 24 is used, no activating agent is required, but an amine base, such as trimethylamine, pyridine, diazobicyclo base, or 5-methoxybenzimidazole, must be used to neutralize the acid generated.

Because there is less concern about premature detritylation in capping steps than in coupling steps, other capping agents such as ammonium salts developed by Beaucage, Caruthers and Wada and co-workers can be used.

For purification of oligomers using polyacrylamide formation reaction, an alternative procedure is to use a fluoride cleavable linker to attach the growing oligomers to the solid support (instead of using the more common base cleavable linkers; besides fluoride cleavable linkers, other non-base cleavable linker such as photo cleavable linkers can also be used) for oligomer synthesis. After synthesis, the oligomers are cleaved from the solid support by treating with fluoride. The crude un-deprotected oligomers are subjected to polymerization reaction conditions. The failure sequences are incorporated into a polymerized material and the full length sequences remain in solution or in polymer matrix. After removal of failure sequences by filtration and extraction of the full length sequences from polymer matrix, the full length sequences are subjected to base de-protection conditions and further purified by recrystallization to remove small molecules resulted from de-deprotection. This alternative purification procedure avoids the possibility of adding nucleophiles to acrylamide functionalities in the base de-protection steps.

Formation of Disulfide Polymer

Thiols may be oxidized to form polymers. One of ordinary skill in the art can determine polymerization conditions that are suitable for such polymerization. For example, for a 1 mmol oligonucleotide synthesis, about 10 mmol to about 100 mmol of a copolymerization agent and about 0.2 mmol to about 2 mmol of a cross-linking copolymerization agent that contains more than 2 thiols in one molecule such as 45 and 56 can be used. Suitably, the mixture is heated in dimethylsulfoxide, for example, to about 90° C. If dimethylsulfoxide is used as a solvent, no additional oxidizing agent is necessary. If another solvent is used, then an oxidizing agent, such as oxygen or others known to those skilled in the art should be added.

Suitable capping agents for purification using formation of a disulfide polymer include compounds of formula (I):

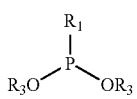
(II)

wherein $R_1$ is halogen, such as Cl, Br or F or a secondary amine, such as

$R_3$ is independently selected from lower alkyl or

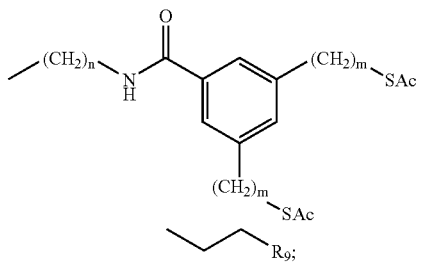

n is an integer from 1 to 5;
m is an integer from 0 to 4;

$R_9$ is an electron withdrawing group such as cyano, $COOR_{10}$, $SO_2Ph$ and $NO_2$; and $R_{10}$ is lower alkyl.

Suitable copolymerization agents include compounds of formula (III):

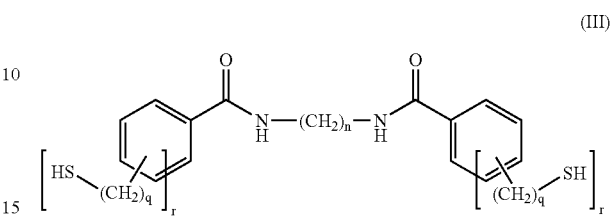
(III)

wherein n is an integer from 1 to 5;
q is independently an integer from 0 to 3; and
r is independently an integer from 1 to 2. Suitably, if r is 1 then the thiol group is at the para-position; if r is 2 then the thiol groups are at the meta-positions.

Thiols 39, 40, 50 and 51 (shown below) are exemplary capping agents for this reaction.

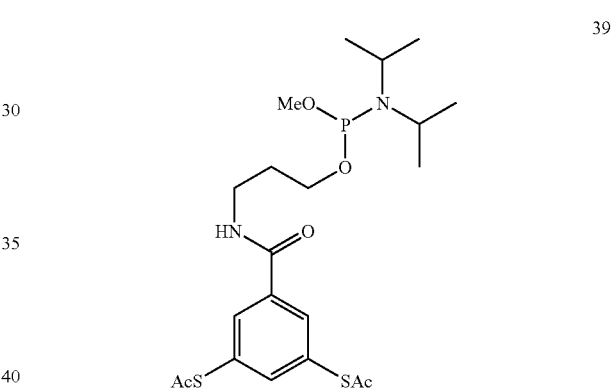
39

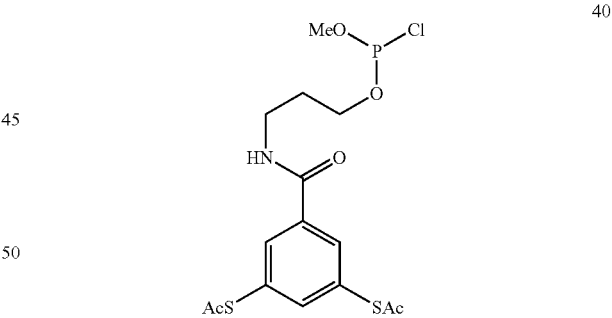
40

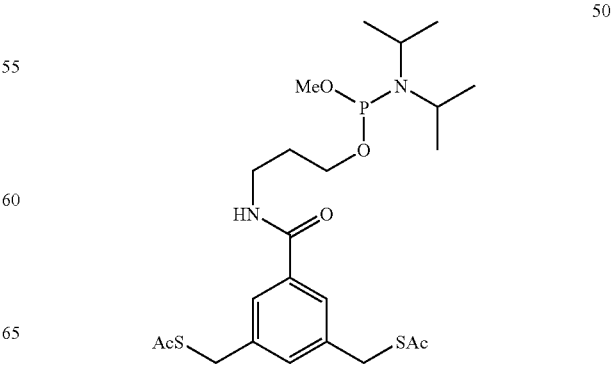
50

-continued

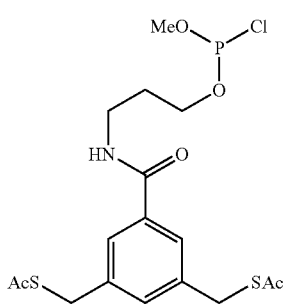
51

Thiols 44, 45, 55 and 56 (shown below) are exemplary copolymerization agents for this reaction.

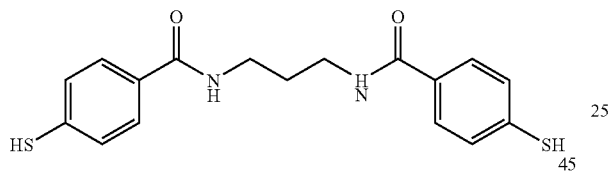
44

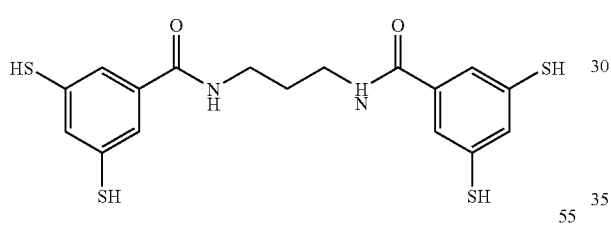
55

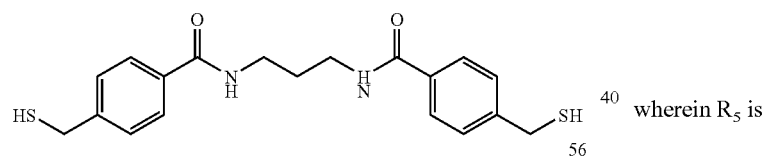
56

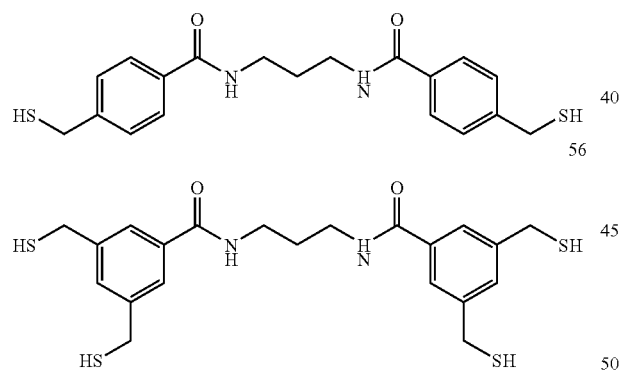

The Sharpless "Click" Reaction

Figure 11:
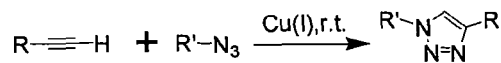
FIG. 11 represents the Sharpless "click" reaction.

The Sharpless "click" reaction is a highly reliable reaction (FIG. 11) and can be performed under aqueous mild conditions. The reaction partners—the terminal alkyne and the alkylazide—are readily accessible stable functional groups. The mild reaction conditions are compatible with many functional groups including those in oligonucleotides. One of ordinary skill in the art can readily determine suitable reaction conditions. For example, for a 1 mmol oligonucleotide synthesis, one can use about 10 mmol to about 100 mmol of each of the copolymerization agents, about 0.05 mmol to about 5.0 mmol $CuSO_4$ and about 0.05 mmol to about 5.0 mmol sodium ascorbate.

Suitable capping agents for purification using the Sharpless "click" reaction include compounds of formula (IV)

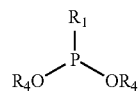
(IV)

wherein $R_1$ is a halogen, such as Cl, Br or F or a secondary amine, such as

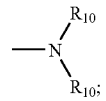

$R_4$ is

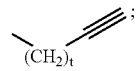

t is an integer from 1 to 3
$R_{10}$ is lower alkyl.
Copolymerization agents are suitably of formula (V):

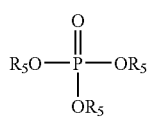
(V)

wherein $R_5$ is

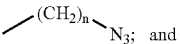
and n is independently an integer from 1 to 5.
A second copolymerization agent is suitably of formula (VI):

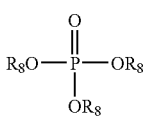
(VI)

wherein $R_8$ is

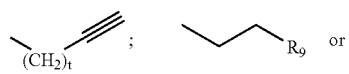

-continued

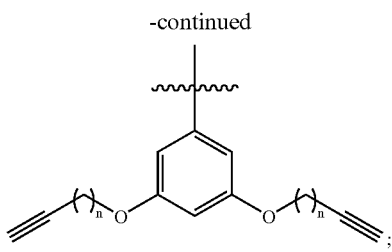

n is independently an integer from 1 to 5, t is an integer from 1 to 3;

$R_9$ is an electron withdrawing group such as cyano, $COOR_{10}$, $SO_2Ph$ and $NO_2$;

$R_{10}$ is lower alkyl

Alkynes 57-60 (shown below) are exemplary capping agents for this reaction.

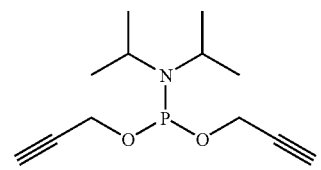
57

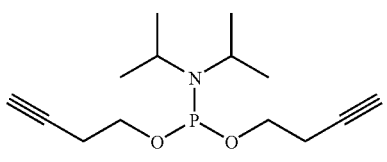
58

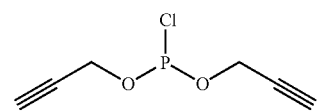
59

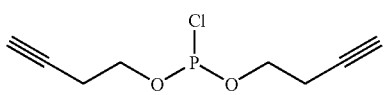
60

Compounds 65 and 66 are exemplary copolymerization agents.

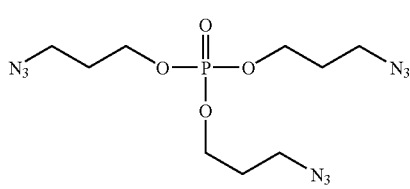
65

-continued

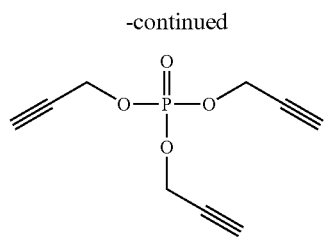
66

Grubbs' ROMP Reaction

Figure 14:
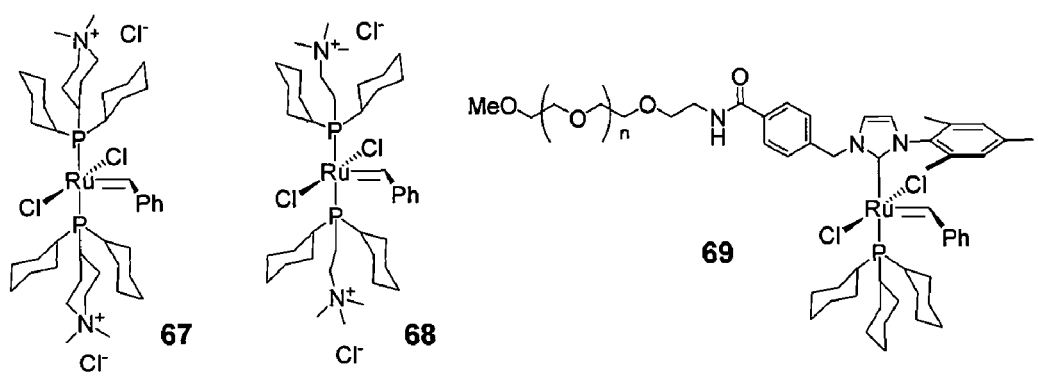
FIG. 14 represents the water soluble Grubbs' ROMP catalysts.

The ring opening metathesis polymerization (ROMP) reaction is also useful for oligonucleotide purification. The polymerization reaction can be performed in aqueous solution using water soluble catalysts (67-69, FIG. 14), and the reaction tolerates a wide range of functional groups. One of ordinary skill in the art can readily determine suitable polymerization conditions. For example, for a 1 mmol oligonucleotide synthesis, one can use about 10 mmol to about 100 mmol of a copolymerization agent, about 0.02 mmol to about 2.0 mmol cross-linking copolymerization agent that contains more than one alkene function such as 78 and 79, and about 0.01 mmol to about 1.0 mmol metathesis catalyst.

Figure 15:
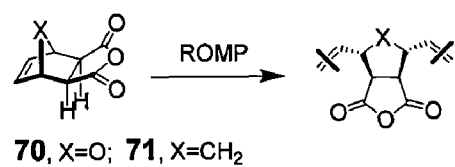
FIG. 15 represents the Grubbs' ROMP reaction.

The substrates for polymerization can be those such as 70 and 71 as shown in FIG. 15. Suitable catalysts for the ROMP purification include, but are not limited to, catalyst 69. After polymerization, the catalyst may be removed by extraction with organic solvents such as $CH_2Cl_2$.

The capping agent is suitably a compound of formula (VII):

(VII)

wherein $R_1$ is halogen, such as Cl, Br or F or a secondary amine, such as

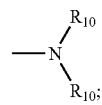

$R_6$ is

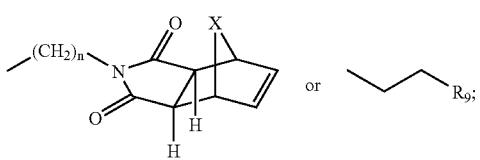

X is independently O or $CH_2$;

$R_9$ is an electron withdrawing group such as cyano, $COOR_{10}$, $SO_2Ph$ and $NO_2$;

$R_{10}$ is lower alkyl; and n is independently an integer from 1 to 5.

A suitable copolymerization agent is a compound of formula (VII)

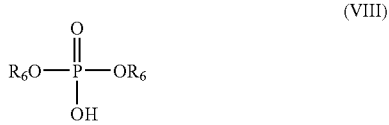
(VIII)

wherein $R_6$ is

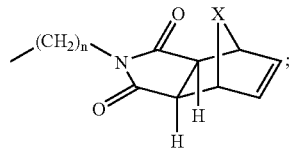

X is independently O or $CH_2$; and
n is independently an integer from 1 to 5.
Compounds 74-77 are exemplary capping agents.

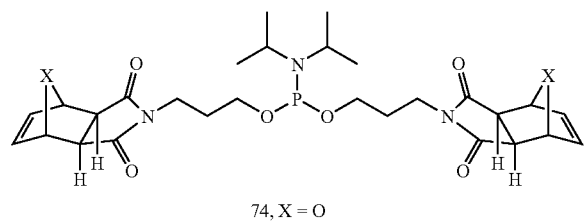

74, X = O
75, X = $CH_2$

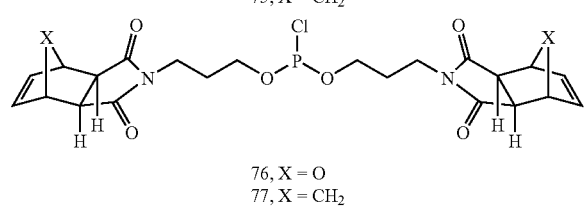

76, X = O
77, X = $CH_2$

Compounds 78, 79, 139, and 140 are exemplary copolymerization agents.

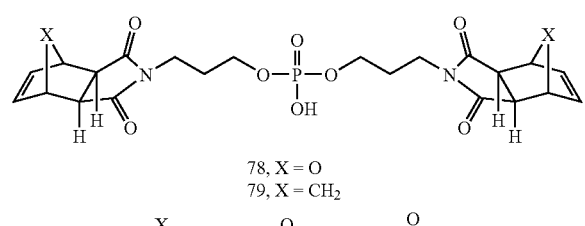

78, X = O
79, X = $CH_2$

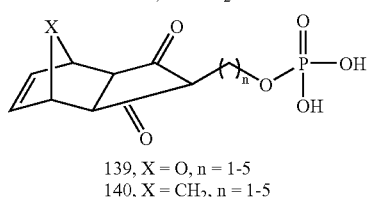

139, X = O, n = 1-5
140, X = $CH_2$, n = 1-5

Conjugate Addition Reaction Between Maleimide and Thiol

The conjugate addition reaction between maleimide and thiol (FIG. 25) is widely used in bioconjugate chemistry. This reaction can be performed in different aqueous buffers in a relatively wide range of pH values (6.5-9) at room temperature, and the reaction is known to be compatible with oligonucleotides. One of ordinary skill in the art can readily determine suitable reaction conditions. For example, for a 1 mmol oligonucleotide synthesis, one can use about 10 mmol to about 100 mmol of a bis-thiol copolymerization agent, about 10 mmol to about 100 mmol of a bis-maleimide copolymerization agent and about 0.2 mmol to about 2.0 mmol of a cross-linking thiol that contains more than 2 thiols in one molecule such as 56 and 86 in a suitable buffer such as phosphate buffered saline buffers and at a suitable temperature such as room temperature and 60° C. Suitable capping reagents are compounds of formula (IX)

(IX)

wherein $R_1$ is halogen, such as Cl, Br or F or a secondary amine, such as

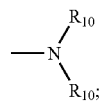

$R_7$ is

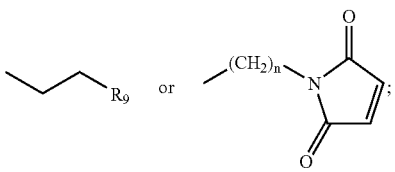

$R_9$ is an electron withdrawing group such as cyano, $COOR_{10}$, $SO_2Ph$ and $NO_2$;
$R_{10}$ is lower alkyl; and
n is independently an integer from 1 to 5.
One of the $R_7$ may also be any functionality that contains 2 or more α,β-unsaturated carbonyl functions Suitable copolymerization agents include compounds of formula (III):

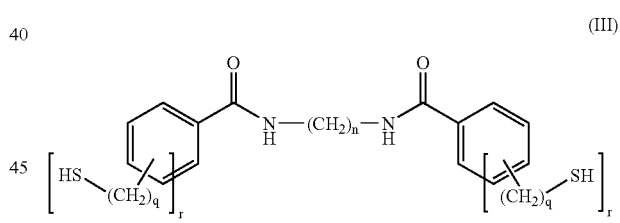
(III)

wherein n is an integer from 1 to 5;
q is independently an integer from 0 to 3; and
r is independently an integer from 1 to 2. Suitably, if r is 1 then the thiol group is at the para-position; if r is 2 then the thiol groups are at the meta-positions.

or a compound of formula (X):

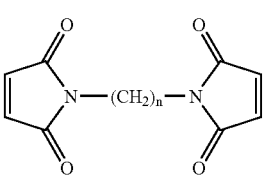
(X)

wherein n is an integer from 1 to 5 or a compound of formula (XI):

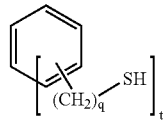

(XI)

wherein q is an integer from 0 to 3; and t is independently an integer from 1 to 3. Suitably, if t is 2 then the thiol groups are para to each other; if t is 3 then the thiol groups are in the meta-positions.

Compounds 82 and 83 are exemplary capping agents.

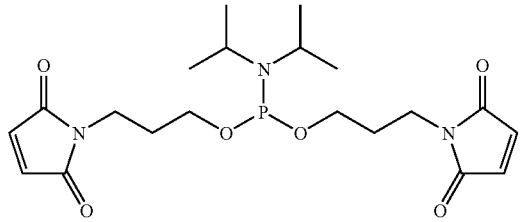

82

83

Compounds 55, 56, 84, 85 and 86 are exemplary copolymerization agents.

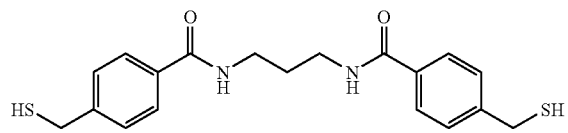

55

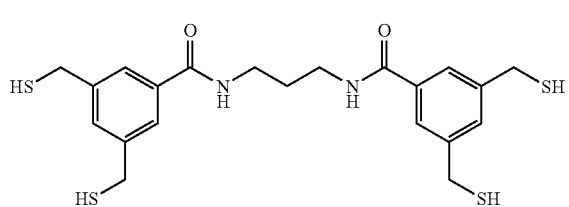

56

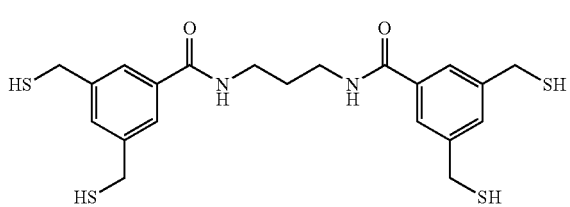

56

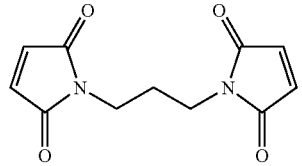

84

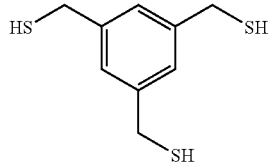

85

86

Amide Formation Between an Ester and an Amine

Amines can react with carboxylic acid derivatives to form amides. This reaction can also be used as the polymerization reaction for purification of oligomers that are synthesized step-wise. One possible such polymerization reaction is shown here:

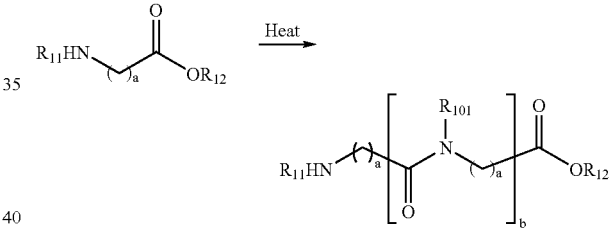

wherein $R_{12}$ is a suitable leaving group, such as $CH_3$, $CH_2CH_3$, $CH_2CH_2OCH_3$, $CH_2CH_2OPh$, or OPh;

$R_{11}$ is selected from hydrogen or lower alkyl₃;

a is an integer from 1 to 6; and b is an undetermined integer.

When using such polymerization reactions to purify oligomers, a suitable condition for a 1 mmol oligomer synthesis, is: about 10 mmol to about 100 mmol of a copolymerization agent and about 0.2 mmol to about 2 mmol of a cross-linking copolymerization agent. The oligonucleotides do not need to be deprotected/cleaved prior to polymerization. The oligonucleotides on solid support can be treated directly under these polymerization conditions. The oligonucleotides will be deprotected/cleaved by the amino group in the copolymerization monomer. The advantages of this method include incorporation of both failure sequences and small molecules resulted from deprotection such as acetyl amide into the polymer and no need for separate deprotection and cleavage step.

Suitable capping agents for purification using the amide bond formation reaction for polymerization includes compounds of formula (XII):

(XII)

[Structure: P with R1, R13O, OR13 substituents]

wherein R₁ is halogen, such as Cl, Br or F or a secondary amine such as

[Structure: N with R10, R10 substituents]

R₁₃ may be

[Structure showing ester group with (CH2)a, OR12, and alternative with R9]

wherein $R_9$ is an electron withdrawing group such as cyano, $COOR_{10}$, $SO_2Ph$ and $NO_2$;

$R_{10}$ is lower alkyl;

$R_{12}$ is a suitable leaving group, such as $CH_3$, $CH_2CH_3$, $CH_2CH_2OCH_3$, $CH_2CH_2OPh$, or OPh; and a is an integer from 1 to 6.

One of the $R_{12}$ groups may also be any functionality that contains 2 or more ester groups.

Suitable copolymerization reagents include but are not limited to

[Structures: R11HN-(CH2)a-C(=Y)-OR12 and R11HN-(CH2)a-SO2-OR12]

wherein $R_{12}$ is a suitable leaving group, such as $CH_3$, $CH_2CH_3$, $CH_2CH_2OCH_3$, $CH_2CH_2OPh$, or OPh;

$R_{11}$ is selected from the group consisting of hydrogen or lower alkyl;

Y=O or S; and a is an integer from 1 to 6.

Suitable cross-linking copolymerization agents include but are not limited to:

[Structure: benzene ring with COOR12 and two CH2NHR11 groups]

wherein $R_{12}$ is a suitable leaving group, such as $CH_3$, $CH_2CH_3$, $CH_2CH_2OCH_3$, $CH_2CH_2OPH$, or OPh;

$R_{11}$ is selected from the group consisting of hydrogen and lower alkyl;

Compounds 141, 142, 143, and 144 are exemplary capping agents for this reaction:

141
[Structure: NC-CH2CH2-O-P(Cl)-O-CH2-C(=O)-OCH3]

142
[Structure: NC-CH2CH2-O-P(N(iPr)2)-O-CH2-C(=O)-OCH3]

143
[Structure: H3CO-C(=O)-CH2-O-P(Cl)-O-CH2-C(=O)-OCH3]

144
[Structure: NC-CH2CH2-O-P(N(iPr)2)-O-CH2CH2-C(=O)-OPh]

Compounds 145, 146, 147, 148 are exemplary copolymerization agents for this reaction:

145
[Structure: H2N-CH2CH2-C(=O)-OCH3]

146
[Structure: H2N-CH2-C(=O)-OCH3]

147
[Structure: H3CHN-CH2-C(=O)-OCH3]

148
[Structure: H2N-CH2-C(=O)-OPh]

Compound 149 is an exemplary cross-linking copolymerization agent for this reaction:

149
[Structure: benzene ring with COOCH3 and two CH2NH2 groups]

Polymerization of Full Length Oligomer

In another embodiment of the present invention, the polymerization reactions can be used to polymerize the desired full-length oligomer sequence. In this embodiment, the capping agent is the normal acetic anhydride or any other suitable capping agent, but at the end of solid phase synthesis, a phosphoramidite that contains a suitable polymerizable functional group is coupled to the end of the oligomer through a cleavable linker. Because failure sequences are all capped with acetic anhydride in each synthetic cycle, only the full length sequence contains the polymerizable functional group. After synthesis, deprotection and cleavage, the crude oligomer is subjected to polymerization; the full length sequence is incorporated into the polymerized material while failure sequences and other impurities remain in solution, which can be removed by filtration or extraction with a buffer. The pure full length sequences are then cleaved from the polymerized material and extracted with a buffer.

Suitable phosphoramidites include compounds 92, 95, 103, 105, 113, 115, 122, 124, 132, 134, 150, 151:

92

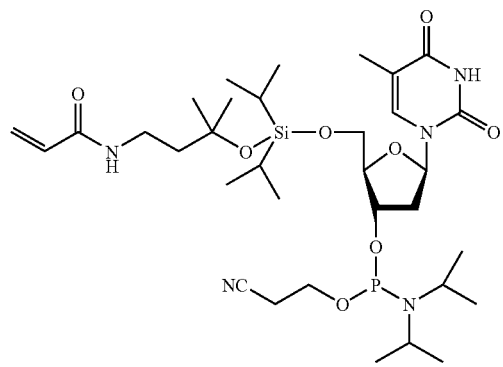

95

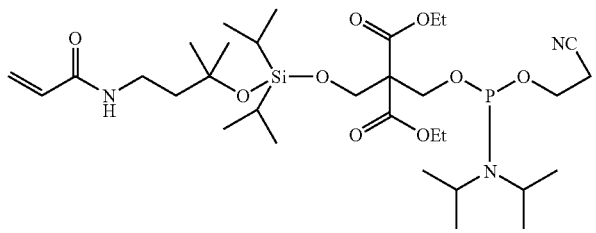

103

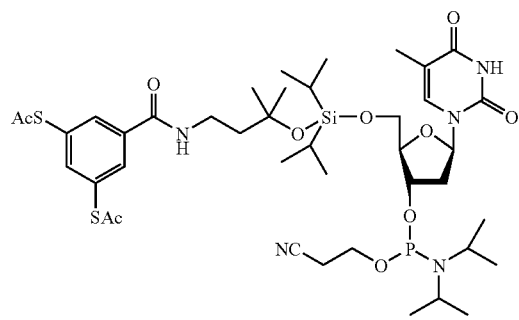

105

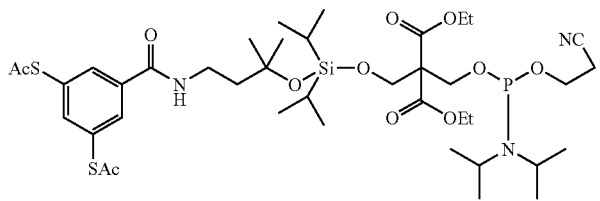

113

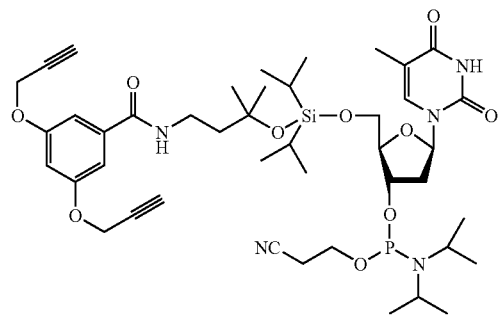

115

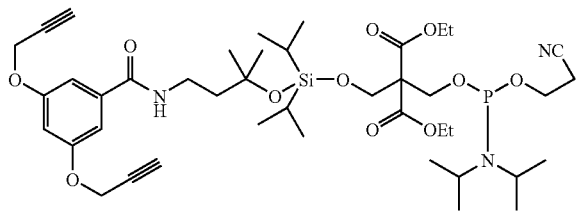

122

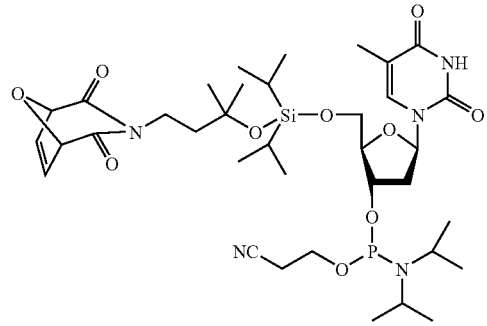

124

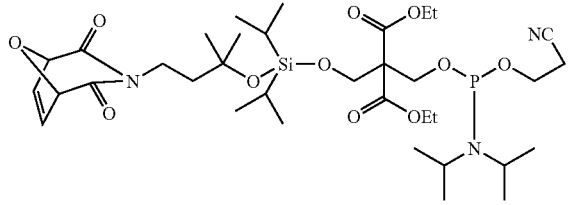

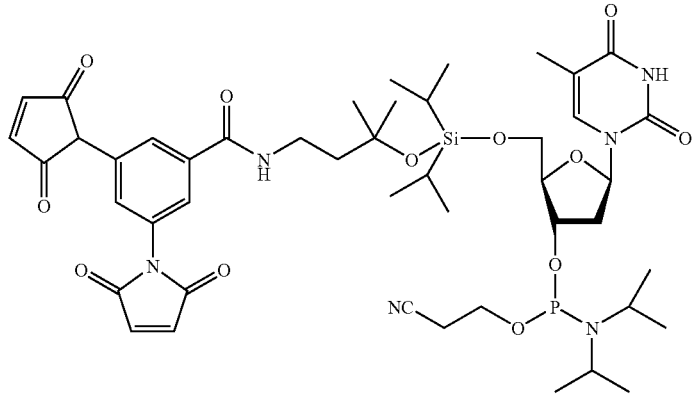

132

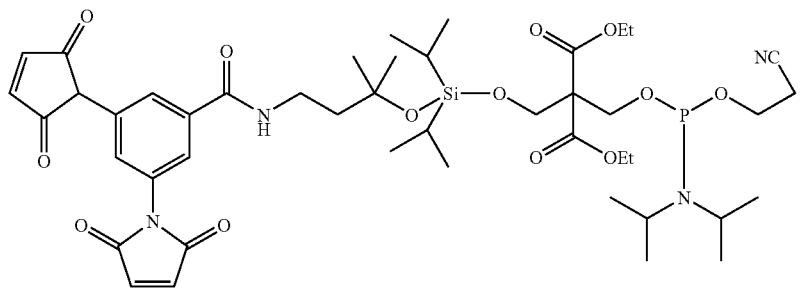

134

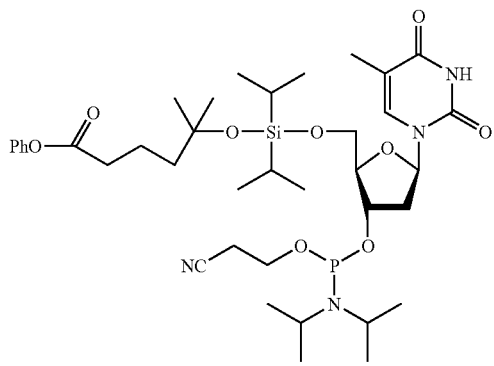

150

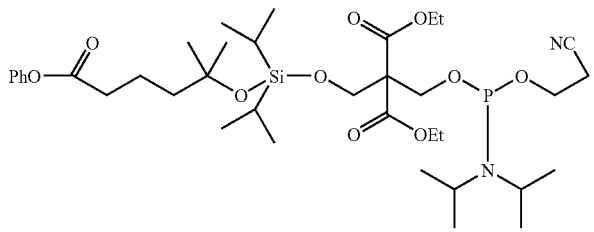

151

Polymerization of Small Molecule Impurities

In yet another embodiment of the present invention, small molecule impurities can be incorporated into the polymerized material and removed along with the failure sequences. In this embodiment, the protecting groups contain a polymerizable functional group, and are also incorporated into the polymerized material. Here, the Sharpless "click" reaction is used as example.

The oligomer is synthesized under standard conditions. However the protecting groups for the nucleobases and the phosphate groups contain a polymerizable functional group. The following phosphoramidite monomers are exemplary:

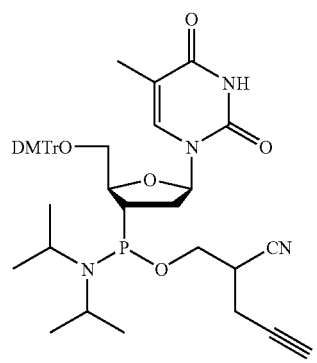

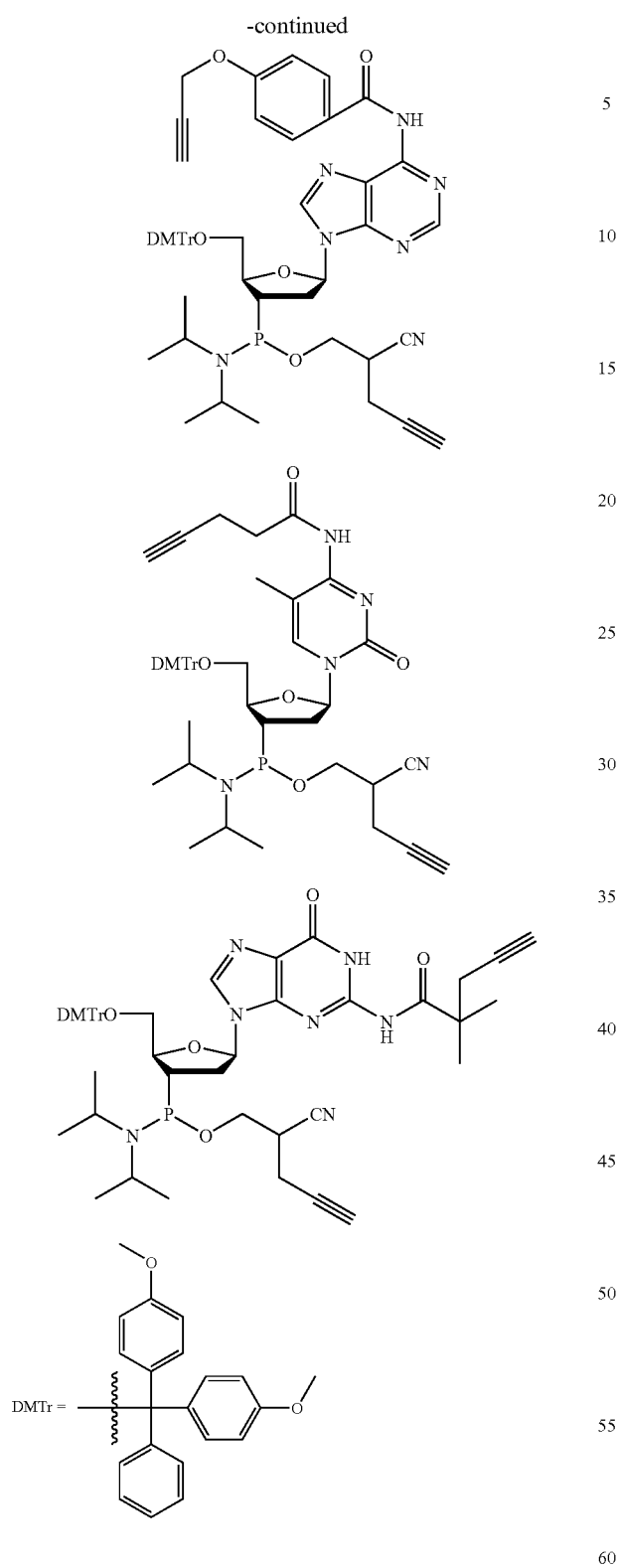

If failure sequences are capped with agents such as 57-60, after cleavage/deprotection, the failure sequence and the small molecules resulted from the protecting groups will all be incorporated into the polymerized material. The full length sequence can be obtained by filtration and extraction. Alternatively, the failure sequences can be capped with a tradi-tional capping agent, such as acetic anhydride and one of the phosphoramidites shown below can be used in the last synthetic cycle.

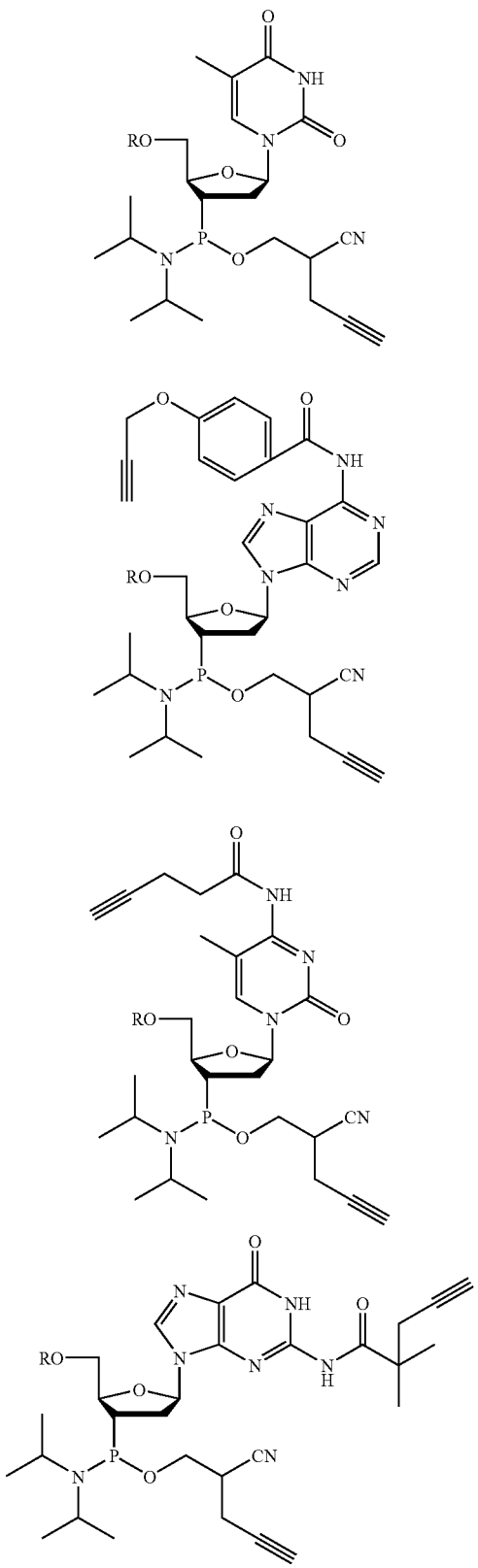

-continued

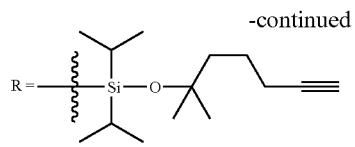

After synthesis and cleavage/deprotection, the full length sequence and the small molecule impurities resulting from protecting groups are incorporated into the polymerized material upon initiation of the polymerization reaction. The failure sequences can be removed by washing. The full length sequences (not small molecules resulted from protecting groups) are then cleaved from the polymer and extracted with buffer.

Kits for Purifying Oligomers

A further embodiment of the present invention is a kit comprising either a capping agent having a polymerizable functional group or a compound having a polymerizable functional group for attaching to the end of the full length oligomer. Kits can further comprise monomers, coupling reagents, polymerization reagents, buffers, cleavage agents, and other components necessary to synthesize and purify an oligomer in accordance with the present invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

It also is specifically understood that any numerical range recited herein includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification.

The following examples are provided to assist in a further understanding of the invention. The particular materials, methods and conditions employed are intended to be illustrative of the invention and are not limiting upon the scope of the invention.

EXAMPLES

Example 1

Purification Via Radical Acrylamide Polymerization of Failure Sequences

Figure 5:
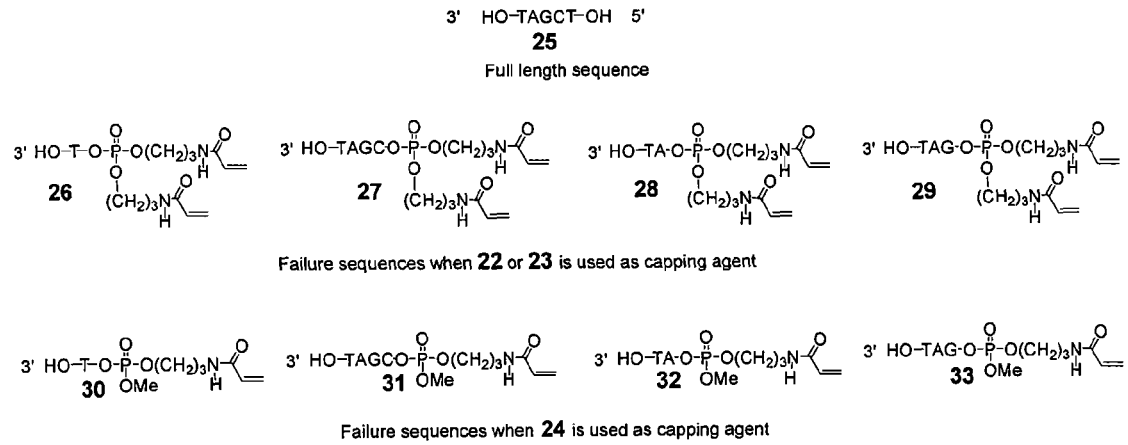
FIG. 5 illustrated the structures of full length sequence and failure sequences when using 22-24 as capping agents.
Figure 6:
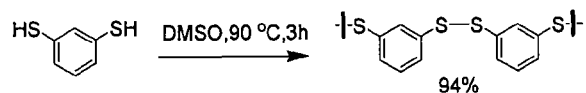
FIG. 6 represents the chemical reaction for formation of disulfide polymer.

After synthesis, the oligonucleotide 25 is cleaved and deprotected under standard basic conditions (for example, $K_2CO_3$, anhydrous methanol, room temperature, 24 hours and concentrated ammonium hydroxide, 60° C.). The crude oligonucleotides are subjected to polymerization conditions, e.g. $(NH_4)_2S_2O_8$/TMEDA/water/r.t./1 h, to incorporate the failure sequences into polymer. The full length sequence 25 (FIG. 5) remains in solution or in the polymer matrix because it does not contain an acrylamide function. Collection of the full length sequence can be achieved by filtration and/or extraction from the polymer gel using a buffer. Impurities resulting from the protecting groups in the synthesis such as acrylonitrile benzamide, acetamide and isobutyramide can be removed by first dissolving the material in sodium acetate buffer and then precipitating the oligonucleotide with 2-propanol (for less than 15-mer) or ethanol (for more than 15-mer) at −10° C. The small organic impurities remain in solution. Alternatively, protecting groups containing acrylamide functions can be used so that all small organic impurities can be removed by polymerization.

Example 2

Figure 7:
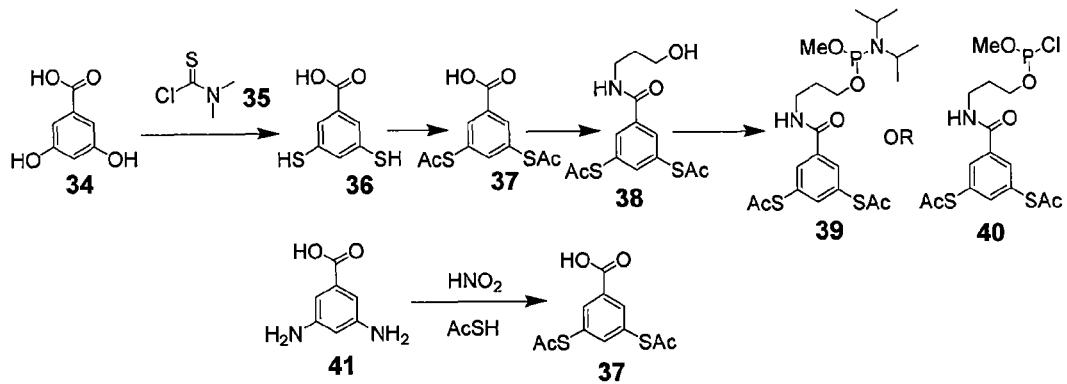
FIG. 7 represents the chemical reaction for synthesis of capping agents 39 and 40.
Figure 8:
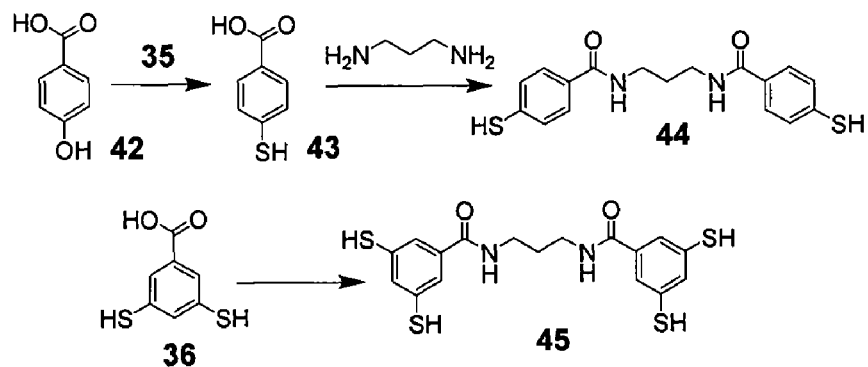
FIG. 8 represents the chemical reaction for synthesis of copolymerization agents 44 and 45.

Synthesis of Thiol Capping Agents and Purification Using Disulfide Formation of Failure Sequences As shown in FIG. 7, 34 is converted to 36 using 35, and acetylated to give 37. Then 37 is converted to 39 or 40 using similar procedures for preparing 22-24. Alternatively, 37 can be synthesized from 41 in one pot as shown in FIG. 7. The thiols 44 and 45, which are required for copolymerization, can also be readily synthesized (FIG. 8).

After synthesis and deprotection/cleavage, the crude oligonucleotide is subjected to polymerization conditions in the presence of 44 and 45 mentioned above. Full length oligonucleotides are collected by filtration and/or extraction. Small organic impurities can be removed by precipitation.

Figure 9:
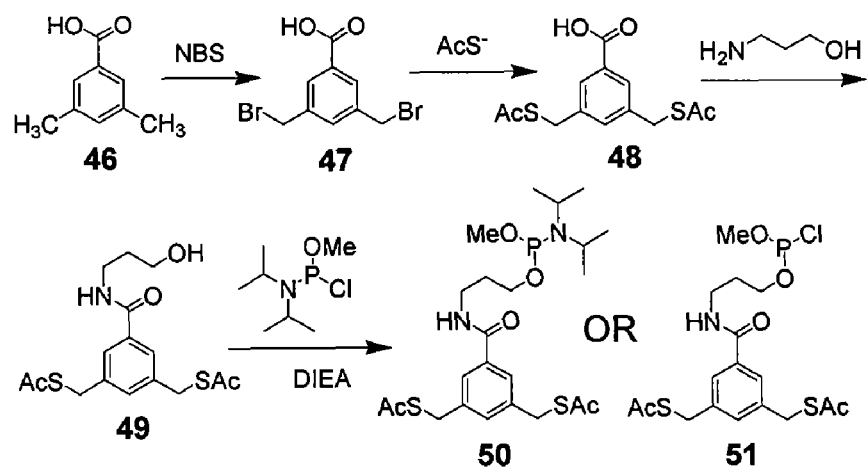
FIG. 9 represents the chemical reaction for synthesis of capping agents 50 and 51.
Figure 10:
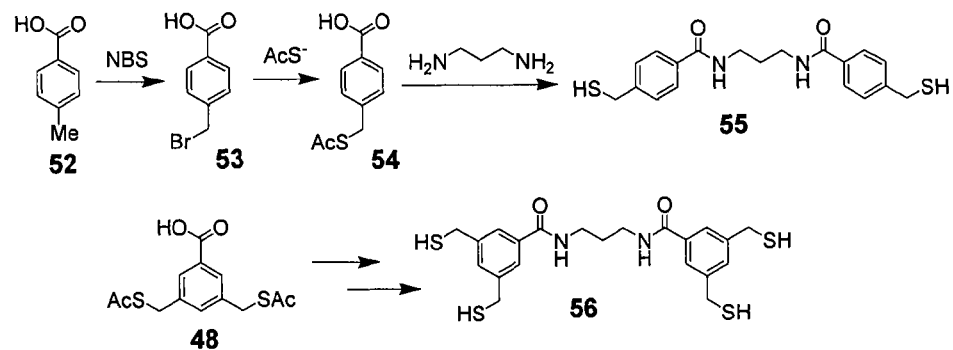
FIG. 10 represents the chemical reaction for synthesis of copolymerization agents 55 and 56.

Alternatively, thiols 50 and 51 can be used for capping failure sequences, and 55 and 56 can be used as copolymerization agents. Their syntheses are illustrated in FIGS. 9 and 10. Compound 48 is prepared from 46 and NBS followed by reacting with AcS⁻ under basic conditions (FIG. 9), which is then converted to the capping agents 50 and 51 using the above described conditions. The copolymerization agents 55 and 56 are readily available as shown in FIG. 10 from compounds 52 and 48. The oligonucleotide synthesis, capping failure sequences with 39, 40, 50 or 51, deprotection/cleavage, polymerization in the presence with 44 and 45 or 55 and 56, purification and analysis of purification results are the same as previously described.

Example 3

Figure 12:
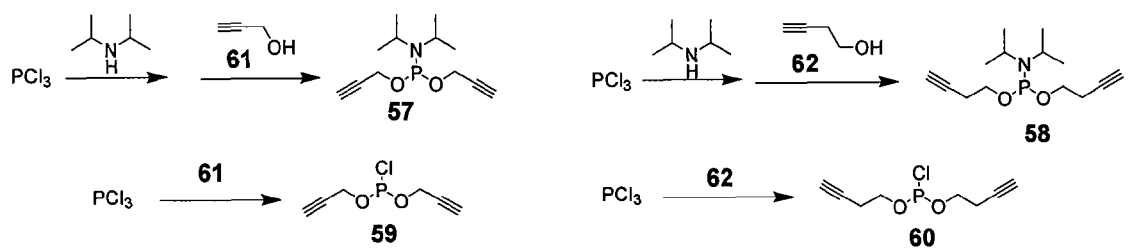
FIG. 12 represents the chemical reaction for synthesis of capping agents 57-60.
Figure 13:
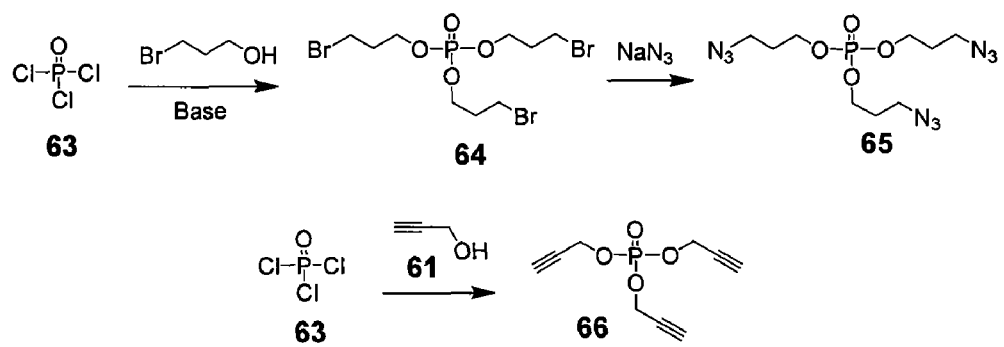
FIG. 13 represents the chemical reaction for synthesis of copolymerization agents 65 and 66.

Synthesis of Capping Agents and Purification via Sharpless "Click" Polymerization of Failure Sequences The capping agents that contain terminal alkynes (57-60) can be easily synthesized according to FIG. 12 from 61 and 62. The polymerization partner 65 is prepared by reacting 63 with 3-bromo-1-propanol to give 64, followed by treating with sodium azide (FIG. 13). The other copolymerization partner 66 is prepared similarly from propargyl alcohol 61 and 63 (FIG. 13). The oligonucleotide synthesis, capping failure sequences with 57-60, deprotection/cleavage, polymerization in the presence of 65 and 66, purification and analysis of purification results are the same as above.

Example 4

Figure 16:
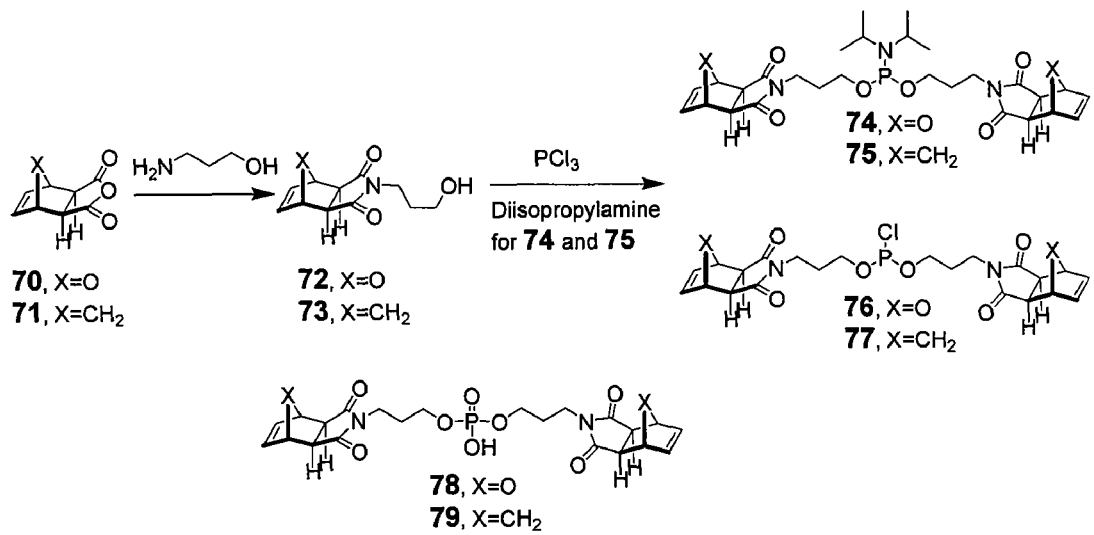
FIG. 16 represents the chemical reaction for synthesis of capping agents 74-77, and the copolymerization agents 78 and 79.
Figure 17:
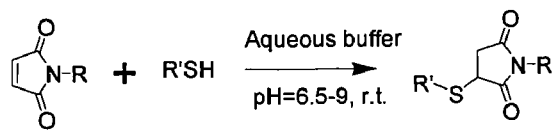
FIG. 17 represents the conjugate addition reaction between maleimide and thiol.

Synthesis of Capping Agents for Purification Via Grubb's Ring Opening Metathasis Polymerization of Failure Sequences The synthesis of the capping agents 74-77 is shown in FIG. 16. Compounds 72 and 73 can be synthesized from 70 (this compound can be prepared readily by stirring the solution of maleic anhydride and furan in ether at room temperature for 12 hours; the exo isomer is formed exclusively as a white precipitate) and 71 (both are commercially available and can be prepared using known procedures) by heating with 3-amino-1-propanol under vacuum in high yields. These two compounds are then converted to the capping agents 74-77 under conditions described above. Suitably, the exo isomers of these compounds are used. The water soluble copolymerization monomers 78 and 79 can be synthesized similarly (FIG. 16). The oligonucleotide synthesis, capping failure sequences with 74-77, deprotection/cleavage, polymerization in the presence of 78 or 79, purification and analysis of purification results are the same as described.

Example 5

Figure 18:
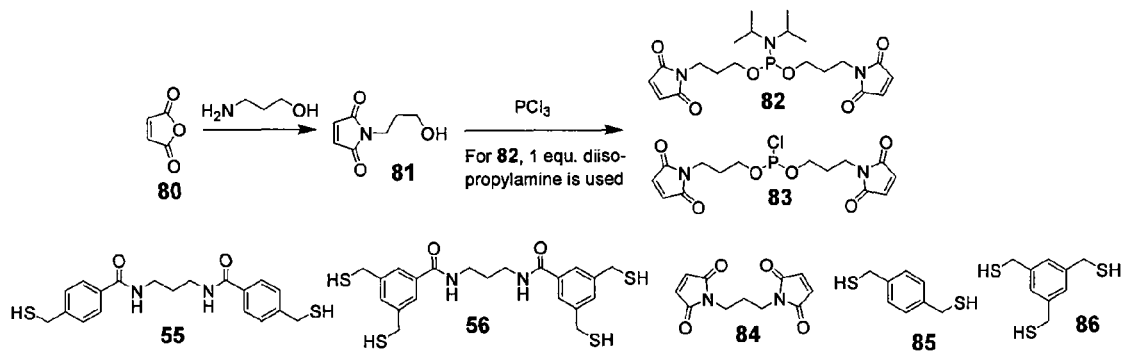
FIG. 18 represents the chemical reaction for synthesis of capping agents 82 and 83, and the copolymerization agents 55 and 56, and 84, 85 and 86.

Synthesis of Capping Agents and Purification Via Conjugate Addition of Maleimide and Thiol of Failure Sequences The synthesis of the capping agents 82 and 83 is shown in FIG. 18. Commercially available maleic anhydride (80) is condensed with 1-amino-3-propanol to give 81, which will be converted to the capping agents 82 and 83 under conditions described earlier. The copolymerization agents 55 and 56 are described earlier; 84-86 can be synthesized easily by one of ordinary skill in the art. After synthesizing oligonucleotide on solid support using standard phosphoramidite chemistry and capping failure sequences with 82 (with activator such as 1H-tetrazole) or 83 (with base such as $Et_3N$), the crude oligonucleotide will be mixed with 55, 56 and 84 to incorporate the failure sequences into polymer using reported conjugate addition conditions. Alternatively, 84-86 may be used for copolymerization.

Example 6

Figure 34:
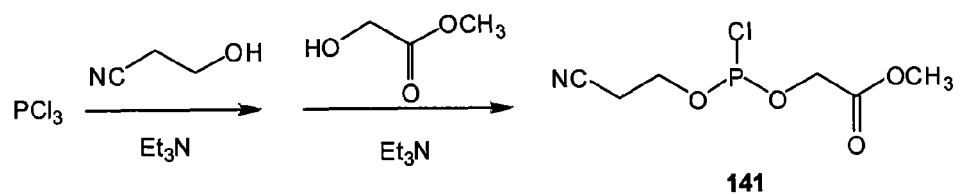
FIG. 34 represents the chemical reaction for the synthesis of capping agent 141.

Synthesis of Capping Agents and Purification Via Amide Bond Formation Reaction to Incorporate Failure Sequences Into Polymer The synthesis of the capping agent 141 is shown in FIG. 34. After synthesizing oligonucleotide on solid support using standard phosphoramidite chemistry and capping failure sequences with 141 the crude oligonucleotide is not cleaved or deprotected. The solid support is then directly treated with copolymerization agent 145 at 60° C. for 12 hours. Then cross-linking copolymerization agent 149 is added and the mixture is then heated to about 90° C. for 6 hours. The failure sequences and small molecules that resulted from deprotection are now incorporated into polymer, while the full length sequence remains in solution or in polymer matrix. Filtration and extraction provide pure full-length sequence.

Example 7

Figure 19:
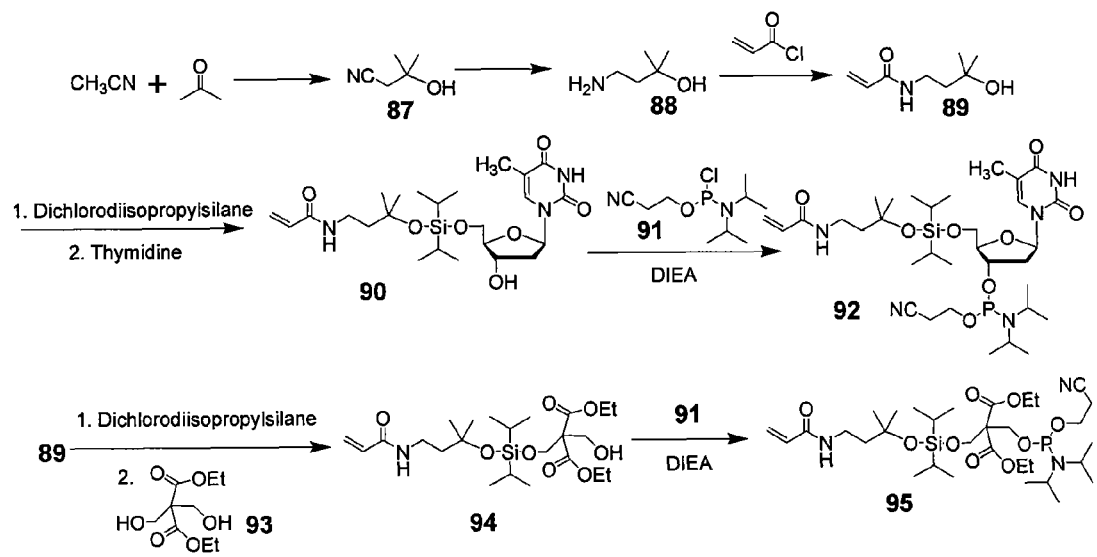
FIG. 19 represents the chemical reaction for synthesis of phosphoramidites 92 and 95.
Figure 20:
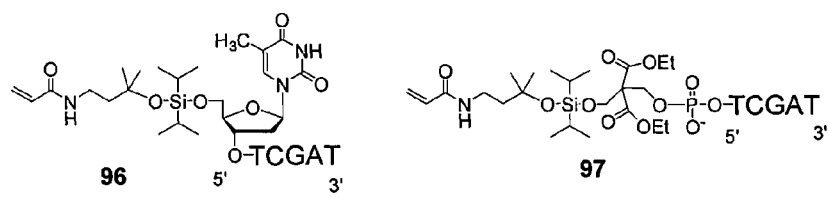
FIG. 20 represents the full length oligonucleotides after deprotection and cleavage using phosphoramidites 92 and 95.

Synthesis of Phosphoramidites 92 and 95 and Purification Via Radical Acrylamide Polymerization of Full-Length Oligomers As shown in FIG. 19, the reaction between acetonitrile and acetone produces 87, which is reduced to the amine 88. Compound 88 reacts with acryloyl chloride to produce 89 in the presence of a base. The tertiary hydroxyl group in 89 is silyated with 1 equivalent dichlorodiisopropylsilane followed by addition of thymidine (suitably protected other nucleobases can also be used, but are not described in this proposal), and this affords 90. The tertiary hydroxyl groups in 89 have two advantages: they stabilize the diisopropylsilyl acetal linkage in 90, and they prevent dimer formation when 89 is mixed with dichlorodiisopropylsilane. Compound 90 is phosphinylated with 91 to produce the target phosphoramidite 92 under standard conditions. 5'-OH oligonucleotide can be produced using 92 for purification. 5'-phosphate oligonucleotides can be purified using the phosphoramidite 95. Phosphoramidite 95 can be synthesized by reacting 89 with 1 equivalent dichlorodiisopropylsilane followed by addition of the commercially available 93 to afford 94, which is phosphinylated to produce 95 under standard conditions (FIG. 19).

Oligonucleotides can be synthesized using a solid phase synthesizer under standard conditions using phosphoramidite methodology. At the end of synthesis, phosphoramidite 92 or 95 is coupled to the 5'-end of oligonucleotide on the synthesizer.

After deprotection and cleavage, oligonucleotide 96 (when 92 is used) or 97 (when 95 is used) is produced, along with failure sequences and small organic impurities. The failure sequences and impurities do not contain the acrylamide functionality. The crude oligonucleotide is then subjected to polymerization conditions, such as acrylamide, N,N'-methylenebisacrylamide, $(NH_4)_2S_2O_8$, TMEDA, r.t., 1 h. The full length sequence 96 or 97 is incorporated into a polymer, and the failure sequences and small organic impurities remain in solution.

Figure 21:
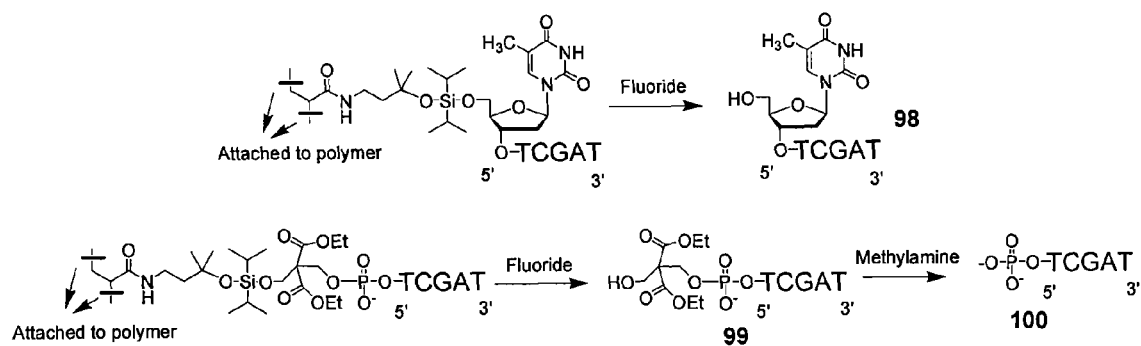
FIG. 21 represents the chemical reaction of cleavage of DNAs 98 and 100 from polymer.

The failure sequences and small organic impurities can be removed by filtration or extraction. The gel that contains the full length sequence is washed with water, DMF and THF. This is followed by treatment with fluoride ion (TBAF or HF/pyridine, r.t. FIG. 21) resulting in oligonucleotide 98 or 99. Oligonucleotide 98 is the target full length sequence with 5'-OH group. Oligonucleotide 99 can be treated with concentrated methylamine to give oligonucleotide 100.

Example 8

Figure 22:
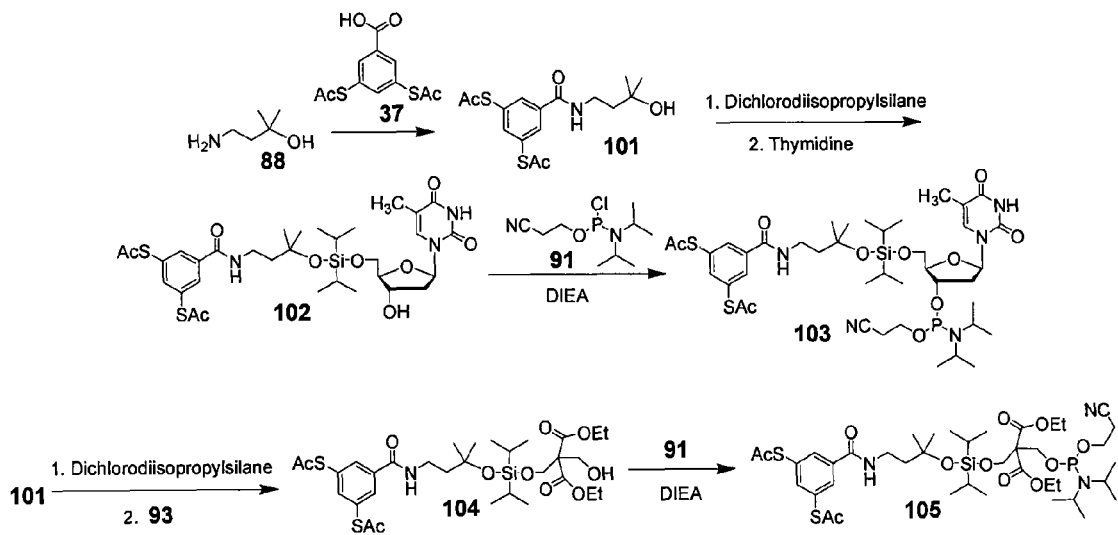
FIG. 22 represents the chemical reaction for synthesis of phosphoramidites 103 and 105.
Figure 23:
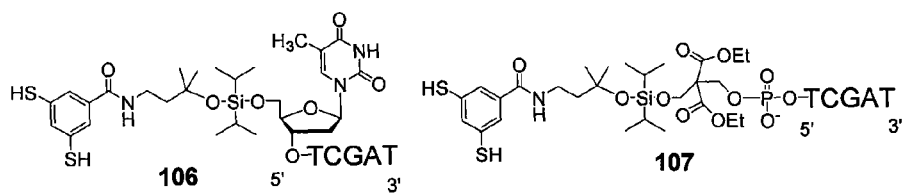
FIG. 23 represents the structures of the oligonucleotides after deprotection and cleavage, using 103 or 105 as the phosphoramidite in the last synthetic cycle in oligonucleotide synthesis.
Figure 24:
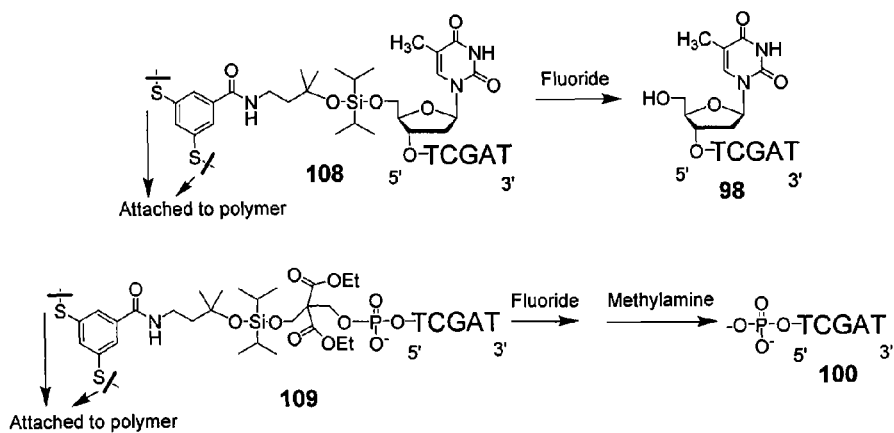
FIG. 24 represents the chemical reaction for the cleavage of DNAs 98 and 100 from polymer.

Synthesis of Phosphoramidites 103 and 105 and Purification Via Disulfide Formation of Full-Length Oligomers Phosphoramidites 103 and 105 are synthesized according to FIG. 22. The amino alcohol 88 is reacted with carboxylic acid 37 (48 can also be used to give 101, which is coupled with thymidine through the diisopropylsilyl acetal linker, and phosphinylated to give phosphoramidite 103. For 5'-phosphate oligonucleotide synthesis, 101 is coupled with 93 using the diisopropylsilyl acetal linker, and phosphinylated to afford phosphoramidite 105. Using 103 or 105 as phosphoramidite in the last synthetic cycle in oligonucleotide synthesis, after deprotection/cleavage, the oligonucleotide has a structure as shown by 106 or 107. Polymerization in the presence of 44 and 45 incorporates 106 or 107 into polymer (see 108 and 109, FIG. 24). After removing failure sequences and other impurities by filtration or extraction, oligonucleotides 98 or 100 are collected as described above (FIG. 24).

Example 9

Figure 25:
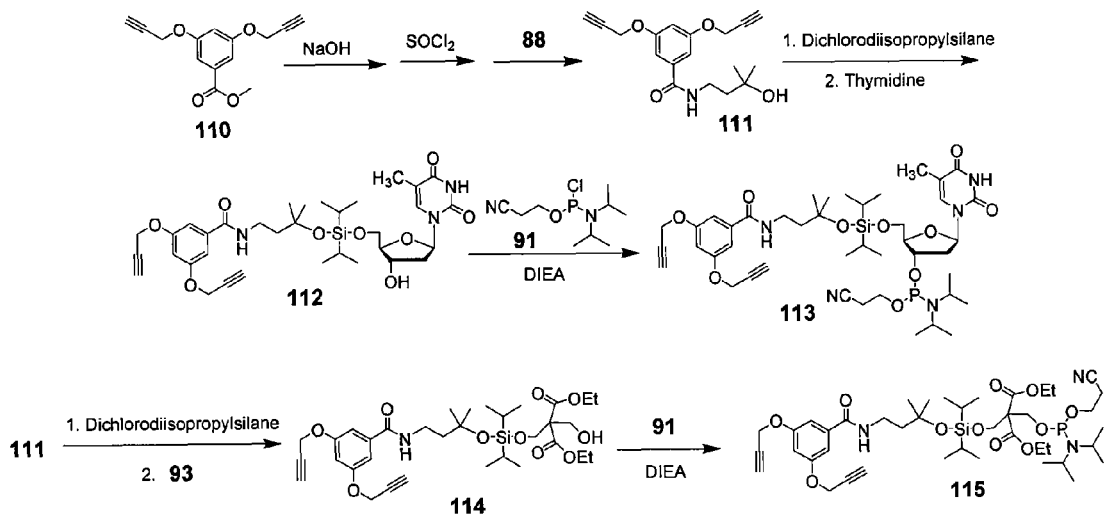
FIG. 25 represents the chemical reaction for synthesis of phosphoramidites 113 and 115.
Figure 26:
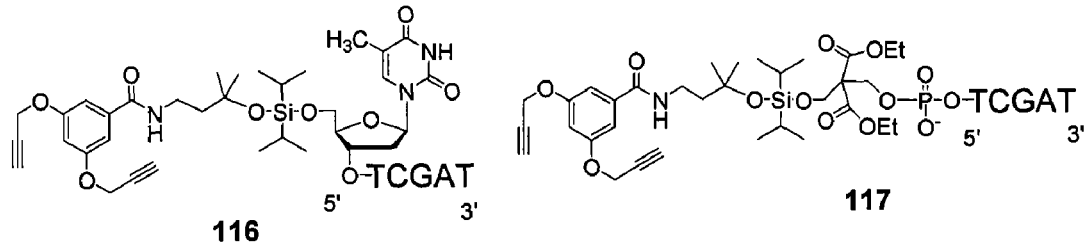
FIG. 26 are the structures of the oligonucleotides after deprotection and cleavage, using 113 or 115 as phosphoramidite in the last synthetic cycle in oligonucleotide synthesis.
Figure 27:
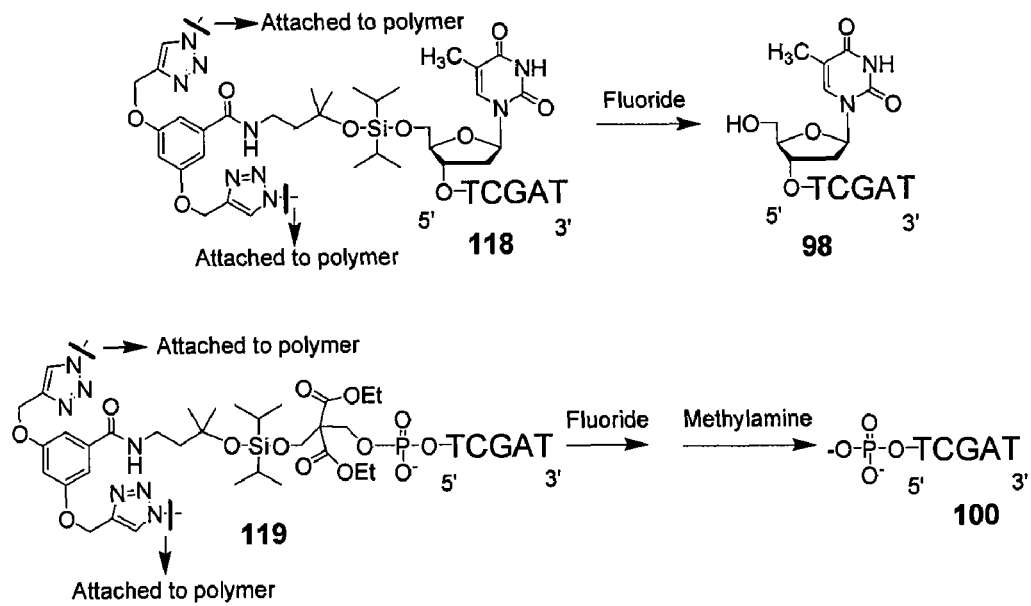
FIG. 27 represents the chemical reaction for cleavage of DNAs 98 and 100 from polymer.

Synthesis of Phosphoramidites 113 and 115 and Purification Via Sharpless "Click" Polymerization of Full-Length Oligomers Phosphoramidites 113 and 115 are synthesized according to FIG. 25. The known alkyne 110 (can be synthesized from inexpensive materials) is hydrolyzed, and coupled with 88 to give 111, which is converted to the thymidine analog 112 and phosphinylated to afford the phosphoramidite 113. The phosphoramidite 115 is synthesized from 111 and 93 in the same way as described for the synthesis of 105. Using 113 or 115 as phosphoramidite in the last synthetic cycle in oligonucleotide synthesis, after deprotection and cleavage, the oligonucleotide has a structure as shown by 116 or 117. Polymerization in the presence of 65 and 66 incorporates 113 or 115 into polymer (see 118 and 119, FIG. 27). After removing failure sequences and other impurities by washing, oligonucleotides 98 or 100 is collected as described above.

Example 10

Figure 28:
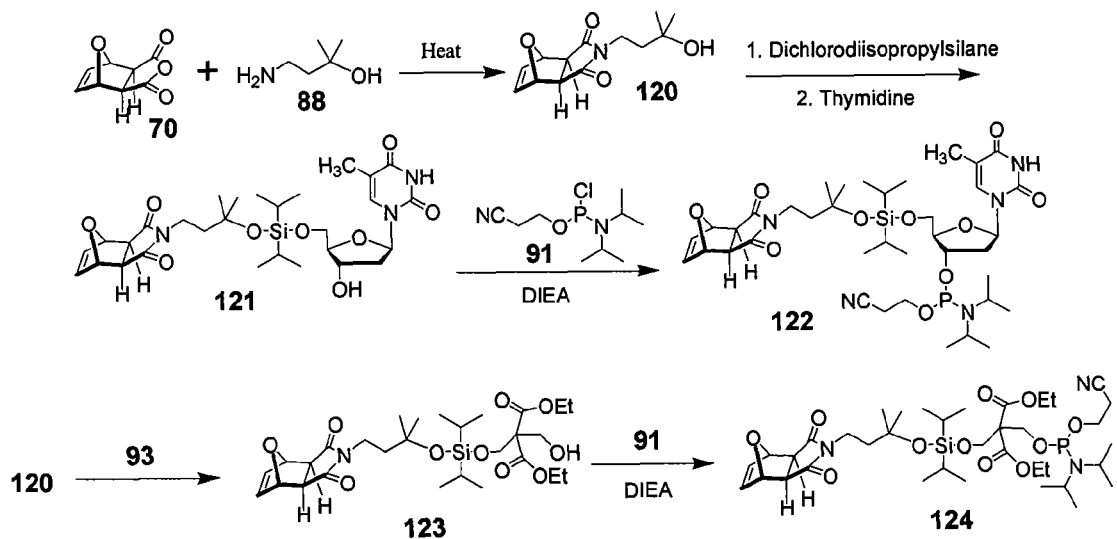
FIG. 28 represents the chemical reaction for synthesis of phosphoramidites 122 and 124.
Figure 29:
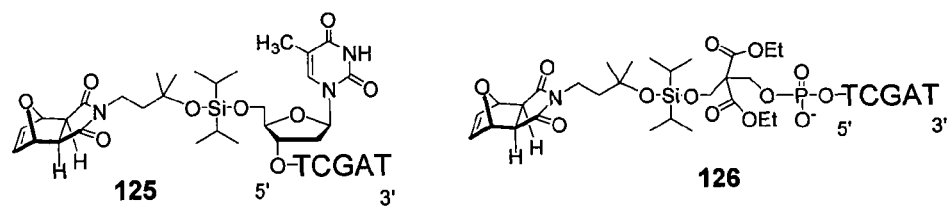
FIG. 29 represents the structures of the oligonucleotides after deprotection and cleavage, using 122 or 124 as phosphoramidite in the last synthetic cycle in oligonucleotide synthesis.
Figure 30:
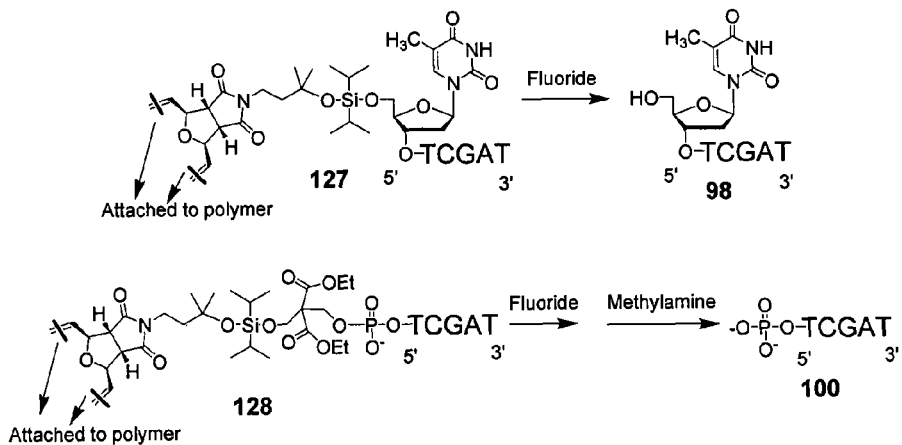
FIG. 30 represents the chemical reaction for cleavage of DNAs 98 and 100 from polymer.

Synthesis of Phosphoramidites 122 and 124 and Purification Using Via Grubb's Ring Opening Metathasis Polymerization of Full-Length Oligomers The required phosphoramidites 122 and 124 are synthesized according to FIG. 28. Compound 70 is reacted with 88 to give 120, which is converted to the thymidine analog 121 and phosphinylated to afford the phosphoramidite 122. The phosphoramidite 124 is synthesized from 120 and 93 in the same way as described for the synthesis of 105. Using 122 or 124 as phosphoramidite in the last synthetic cycle in oligonucleotide synthesis, after deprotection and cleavage, the oligonucleotide has a structure as shown by 125 or 126. Polymerization in the presence of 78 incorporates 125 or 126 into polymer (see 127 and 128, FIG. 30). After removing failure sequences and other impurities, oligonucleotides 98 or 100 are collected as described above.

Example 11

Figure 31:
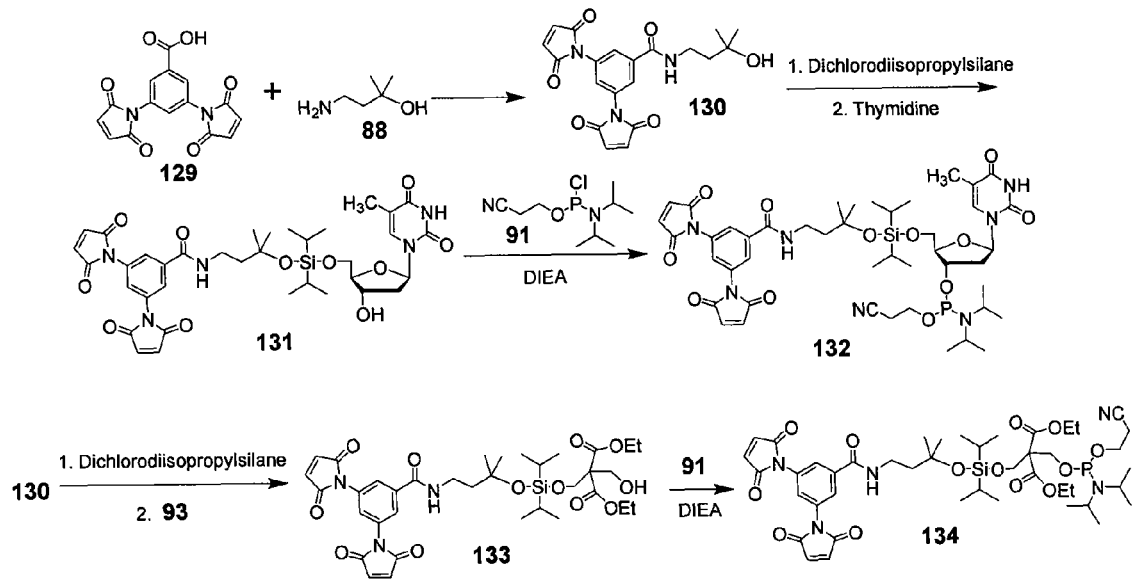
FIG. 31 represents the chemical reaction for synthesis of phosphoramidites 132 and 134.
Figure 32:
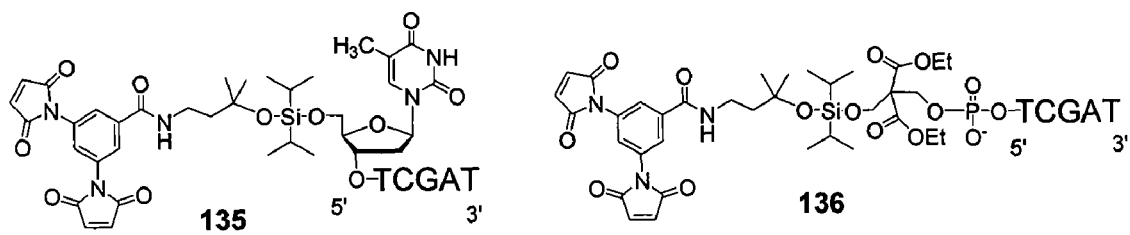
FIG. 32 represents the chemical structures for the oligonucleotides after deprotection and cleavage, using 132 or 134 as phosphoramidite in the last synthetic cycle in oligonucleotide synthesis.
Figure 33:
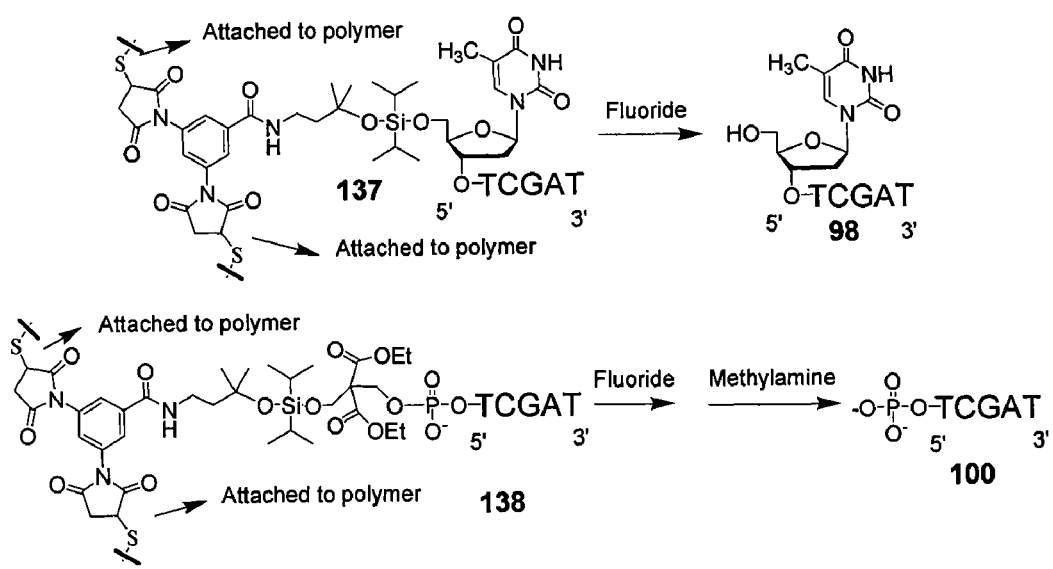
FIG. 33 represents the chemical reaction for the cleavage of DNAs 98 and 100 from polymer.

Synthesis of Phosphoramidites 132 and 134 and Purification Via Conjugate Addition of Maleimide and Thiol Full-Length Oligomers The required phosphoramidites 132 and 134 are synthesized according to FIG. 31. Compound 129 (which can be prepared from 3,5-diaminobenzoic acid and maleic anhydride) is reacted with 88 to give 130, which is converted to the thymidine analog 131 and phosphinylated to afford the phosphoramidite 132. The phosphoramidite 134 is synthesized from 130 and 93 in the same way as described for the synthesis of 105. Using 132 or 134 as phosphoramidite in the last synthetic cycle in oligonucleotide synthesis, after deprotection and cleavage, the oligonucleotide has a structure as shown by 135 or 136 (FIG. 32). Polymerization in the presence of 84, 85 and 86 incorporates 135 or 136 into polymer (see 137 and 138, FIG. 33). After removing failure sequences and other impurities, oligonucleotides 98 or 100 are collected as described above.

Example 12

Figure 35:
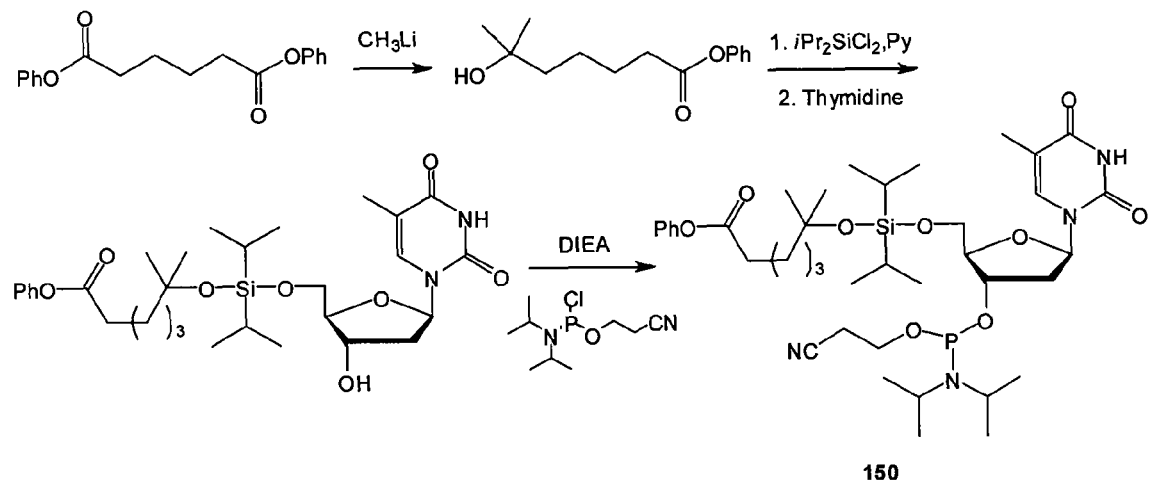
FIG. 35 represents the chemical reaction for the synthesis of phosphoramidites 150.

Synthesis of Phosphoramidites and Purification Via Incorporation of Full Length Sequence into Polymer using the Amide Bond Formation Reaction Phosphoramidite 150 is synthesized according to FIG. 35. Using phosphoramidite 150 in the last synthetic cycle, the oligonucleotide synthesized on the solid support has structure 152:

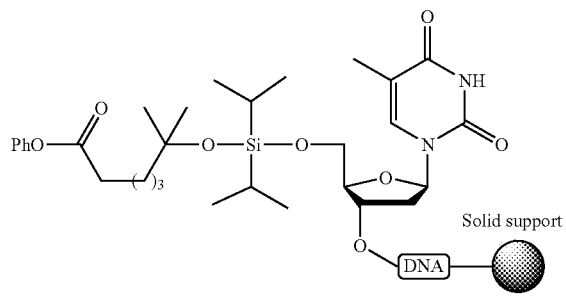

Structure 152 is then treated with 146 at about 60° C. for about 6 hours, without standard basic deprotection or cleavage. During the reaction, the phenoxide in the full length sequence is displaced by the amino group in 146. Next, the cross-linking copolymerization reagent 149 is added and the mixture heated to 90° C. for about 6 hours. During this reaction the oligonucleotides are cleaved from the solid support, all protecting groups are removed, and the full length sequence and the small molecules resulting from the protecting groups are incorporated into a polymerized material. Pure full length sequence will be collected by treating with fluoride as described above.

All patents, publications and references cited herein are hereby fully incorporated by reference. In case of conflict between the present disclosure and incorporated patents, publications and references, the present disclosure should control.

The invention claimed is:

1. A method of purifying an oligomer comprising:
 capping any failure sequences produced during synthesis with a capping agent having a polymerizable functional group;
 polymerizing the capped failure sequences; and
 separating the polymerized material from the full-length oligomer;
 wherein the capping agent is a compound of formula (IV):

wherein $R_1$ is a halogen or a secondary amine;
$R_4$ is

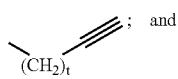

t is an integer from 1 to 3.

* * * * *